United States Patent
Marcotte et al.

(10) Patent No.: US 8,100,870 B2
(45) Date of Patent: Jan. 24, 2012

(54) ADJUSTABLE HEIGHT GASTRIC RESTRICTION DEVICES AND METHODS

(75) Inventors: Amy L. Marcotte, Mason, OH (US); David Krumanaker, Cincinnati, OH (US); Kevin Felder, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 985 days.

(21) Appl. No.: 11/956,729

(22) Filed: Dec. 14, 2007

(65) Prior Publication Data
US 2009/0157106 A1 Jun. 18, 2009

(51) Int. Cl.
*A61M 37/00* (2006.01)
(52) U.S. Cl. ............ 604/288.02; 606/151; 604/288.01; 604/93.01
(58) Field of Classification Search ............... 600/37; 604/93, 175, 93.01–288.04; 606/151, 201–202, 606/153, 157
See application file for complete search history.

(56) References Cited

U.S. PATENT DOCUMENTS

| | | |
|---|---|---|
| RE3,036 E | 7/1868 | Shunk |
| RE3,037 E | 7/1868 | Tucker |
| RE3,115 E | 9/1868 | Lewis |
| RE3,187 E | 11/1868 | Winchester |
| RE3,322 E | 3/1869 | Murch |
| 236,373 A | 1/1881 | Spilman |
| 322,388 A | 7/1885 | Lord |
| 400,401 A | 3/1889 | Gutzkow |
| D23,637 S | 9/1894 | Casad |
| D24,900 S | 11/1895 | Clemecet |
| D25,318 S | 3/1896 | Perky |
| D27,151 S | 6/1897 | Moulten |
| D29,715 S | 11/1898 | Wheeler |
| D29,745 S | 11/1898 | Bunker |
| D29,885 S | 12/1898 | Gillespie et al. |
| D30,690 S | 5/1899 | Schwedtmann |
| D30,966 S | 6/1899 | Howe |
| D31,230 S | 7/1899 | Hogan |
| 689,758 A | 12/1901 | Shaw |
| 724,913 A | 4/1903 | Montgomery |

(Continued)

FOREIGN PATENT DOCUMENTS

CA 1059035 7/1979

(Continued)

OTHER PUBLICATIONS

European Search Report, Application No. 09250497.6, Issued May 13, 2009, 10 pages.

(Continued)

*Primary Examiner* — Corrine M McDermott
*Assistant Examiner* — Todd J Scherbel
(74) *Attorney, Agent, or Firm* — Nutter McClennen & Fish LLP

(57) ABSTRACT

Methods and devices are provided for adjusting the height of devices in a gastric restriction system. In general, the methods and devices allow one or more implantable housings coupled to an implantable restriction device to have an adjustable height. The housing can include, for example, a fill port housing, a sensor housing, and any other type of housing that can be used in an implantable restriction system and desired to have an adjustable height. The housing can lower in profile over time, e.g., as the patient loses weight, thereby maintaining the housing in a generally predictable location where it can be found and accessed.

16 Claims, 13 Drawing Sheets

U.S. PATENT DOCUMENTS

| | | |
|---|---|---|
| 899,477 A | 9/1908 | Williams |
| 926,197 A | 6/1909 | Kim |
| 953,875 A | 4/1910 | Waring |
| 991,192 A | 5/1911 | Batttenfeld |
| 1,087,988 A | 2/1914 | Sheldon |
| 1,210,701 A | 1/1917 | Ryden |
| 1,219,296 A | 3/1917 | Hahn |
| 1,224,355 A | 5/1917 | Brown |
| 1,263,914 A | 4/1918 | Martin |
| 1,310,290 A | 7/1919 | Piechowicz |
| 1,384,873 A | 7/1921 | Strickland |
| 1,421,507 A | 7/1922 | Lindberg |
| 1,551,525 A | 8/1925 | Hamer |
| 1,560,973 A | 11/1925 | Cheron |
| 1,620,633 A | 3/1927 | Colvin |
| 1,623,403 A | 4/1927 | Friel |
| 1,689,085 A | 10/1928 | Russell et al. |
| 1,764,071 A | 6/1930 | Foulke |
| 1,782,704 A | 11/1930 | Woodruff |
| 1,807,107 A | 5/1931 | Sternberch |
| 1,865,446 A | 7/1932 | Sears |
| 1,822,338 A | 10/1932 | Reed et al. |
| 1,924,781 A | 8/1933 | Gaiser |
| 2,027,875 A | 1/1936 | Odend'hal |
| 2,063,430 A | 12/1936 | Graser |
| 2,099,160 A | 11/1937 | Charch |
| 2,105,127 A | 1/1938 | Petrone |
| 2,106,192 A | 1/1938 | Saville |
| 2,143,429 A | 1/1939 | Auble |
| 2,166,603 A | 7/1939 | Menzer |
| 2,168,427 A | 8/1939 | McConkey |
| 2,174,525 A | 10/1939 | Padernal |
| 2,177,564 A | 10/1939 | Havill |
| 2,178,463 A | 10/1939 | Bahnson |
| 2,180,599 A | 11/1939 | Menasco |
| 2,203,460 A | 6/1940 | Fieber |
| 2,206,038 A | 7/1940 | Lang Ford |
| 2,216,374 A | 10/1940 | Martin |
| 2,223,699 A | 12/1940 | Norgren |
| 2,225,145 A | 12/1940 | Baumbach |
| 2,225,880 A | 12/1940 | Montelius |
| 2,261,060 A | 10/1941 | Giesler |
| 2,261,355 A | 11/1941 | Flynn |
| 2,295,539 A | 9/1942 | Beach |
| 2,303,108 A | 11/1942 | Blackburn |
| 2,303,502 A | 12/1942 | Rous |
| 2,318,819 A | 5/1943 | Verson |
| 2,327,407 A | 8/1943 | Edyvean |
| 2,327,615 A | 8/1943 | Ankarlo |
| 2,354,571 A | 7/1944 | Blain |
| 2,426,392 A | 8/1947 | Fennema |
| 2,426,817 A | 9/1947 | Charlton et al. |
| 2,440,260 A | 4/1948 | Gall |
| 2,442,573 A | 6/1948 | Stafford |
| 2,453,217 A | 11/1948 | Gregg et al. |
| 2,455,859 A | 12/1948 | Foley |
| 2,477,922 A | 8/1949 | Emery et al. |
| 2,478,876 A | 8/1949 | Nelson |
| 2,482,392 A | 9/1949 | Whitaker |
| 2,494,881 A | 1/1950 | Kost |
| 2,509,210 A | 5/1950 | Clark |
| 2,509,673 A | 5/1950 | Church |
| 2,511,765 A | 6/1950 | Bradbury |
| 2,520,056 A | 8/1950 | Pozun |
| 2,521,976 A | 9/1950 | Hays |
| 2,533,924 A | 12/1950 | Foley |
| 2,538,259 A | 1/1951 | Merriman |
| 2,581,479 A | 1/1952 | Grashman |
| 2,600,324 A | 6/1952 | Rappaport |
| 2,606,003 A | 8/1952 | McNeill |
| 2,615,940 A | 10/1952 | Williams |
| 2,632,447 A | 3/1953 | Dobes |
| 2,639,342 A | 5/1953 | Cope |
| 2,640,119 A | 5/1953 | Bradford, Jr. |
| 2,641,742 A | 6/1953 | Wolfe |
| 2,651,304 A | 9/1953 | Browner |
| 2,665,577 A | 1/1954 | Sanowskis |
| 2,673,999 A | 4/1954 | Shey |
| 2,676,609 A | 4/1954 | Pfarrer |
| 2,684,118 A | 7/1954 | Osmun |
| 2,689,611 A | 9/1954 | Martinson |
| 2,697,435 A | 12/1954 | Ray |
| 2,723,323 A | 11/1955 | Niemi |
| 2,734,992 A | 2/1956 | Elliot et al. |
| 2,740,007 A | 3/1956 | Amelang |
| 2,740,853 A | 4/1956 | Hatman, Jr. |
| 2,742,323 A | 4/1956 | Shey |
| 2,747,332 A | 5/1956 | Morehouse |
| 2,753,876 A | 7/1956 | Kurt |
| 2,756,883 A | 7/1956 | Schreck |
| 2,756,983 A | 7/1956 | Furcini |
| 2,761,603 A | 9/1956 | Fairchild |
| 2,773,312 A | 12/1956 | Peck |
| 2,783,728 A | 3/1957 | Hoffmann |
| 2,787,875 A | 4/1957 | Johnson |
| 2,793,379 A | 5/1957 | Moore |
| 2,795,460 A | 6/1957 | Bletcher |
| 2,804,514 A | 8/1957 | Peters |
| 2,822,113 A | 2/1958 | Joiner, Jr. |
| 2,831,478 A | 4/1958 | Uddenberg et al. |
| 2,864,393 A | 12/1958 | Drake |
| 2,865,541 A | 12/1958 | Hicks |
| 2,870,024 A | 1/1959 | Martin |
| 2,883,995 A | 4/1959 | Bialous et al. |
| 2,886,355 A | 5/1959 | Wurzel |
| 2,895,215 A | 7/1959 | Neher et al. |
| 2,899,493 A | 8/1959 | Levine |
| 2,902,861 A | 9/1959 | Frost et al. |
| 2,923,531 A | 2/1960 | Bauer et al. |
| 2,924,263 A | 2/1960 | Landis |
| 2,924,432 A | 2/1960 | Arps et al. |
| 2,930,170 A | 3/1960 | Holsman et al. |
| 2,938,592 A | 5/1960 | Charske et al. |
| 2,941,338 A | 6/1960 | Santschi |
| 2,943,682 A | 7/1960 | Ingram, Jr. et al. |
| 2,958,781 A | 11/1960 | Marchal et al. |
| 2,961,479 A | 11/1960 | Bertling |
| 2,976,355 A | 3/1961 | Levine |
| 2,976,686 A | 3/1961 | Stelzer |
| 2,977,876 A | 4/1961 | Meyers |
| 2,986,715 A | 5/1961 | Church et al. |
| 2,989,019 A | 6/1961 | Van Sciver, II |
| 3,010,692 A | 11/1961 | Jentoft |
| 3,013,234 A | 12/1961 | Bourns |
| 3,018,791 A | 1/1962 | Knox |
| 3,034,356 A | 5/1962 | Bieganski |
| 3,040,800 A | 6/1962 | Hartley |
| 3,054,618 A | 9/1962 | Abrams et al. |
| 3,060,262 A | 10/1962 | Hoer |
| 3,070,373 A | 12/1962 | Mathews et al. |
| 3,082,414 A | 3/1963 | Papaminas |
| 3,085,577 A | 4/1963 | Berman et al. |
| 3,096,410 A | 7/1963 | Anderson |
| 3,099,262 A | 7/1963 | Bigliano |
| 3,125,028 A | 3/1964 | Rohde |
| 3,126,029 A | 3/1964 | Englesson |
| 3,129,072 A | 4/1964 | Cook et al. |
| 3,135,914 A | 6/1964 | Callan et al. |
| 3,144,017 A | 8/1964 | Muth |
| 3,151,258 A | 9/1964 | Sonderegger et al. |
| 3,153,460 A | 10/1964 | Raskin |
| 3,161,051 A | 12/1964 | Perry, Jr. |
| 3,167,044 A | 1/1965 | Henrickson |
| 3,171,549 A | 3/1965 | Orloff |
| 3,172,700 A | 3/1965 | Haas |
| 3,173,269 A | 3/1965 | Imbertson |
| 3,182,494 A | 5/1965 | Beatty et al. |
| 3,187,181 A | 6/1965 | Keller |
| 3,187,745 A | 6/1965 | Baum et al. |
| 3,190,388 A | 6/1965 | Moser et al. |
| 3,205,547 A | 9/1965 | Rieske |
| 3,208,255 A | 9/1965 | Burk |
| 3,209,570 A | 10/1965 | Hills |
| 3,221,468 A | 12/1965 | Casey |
| 3,228,703 A | 1/1966 | Wilson |
| 3,229,684 A | 1/1966 | Nagumo et al. |
| 3,236,088 A | 2/1966 | Moller |

| | | | | | | |
|---|---|---|---|---|---|---|
| 3,238,624 A | 3/1966 | McCabe | | 3,512,517 A | 5/1970 | Kadish et al. |
| 3,240,510 A | 3/1966 | Spouge | | 3,514,919 A | 6/1970 | Ashton et al. |
| 3,245,642 A | 4/1966 | Dicke | | 3,516,220 A | 6/1970 | Buford et al. |
| 3,255,568 A | 6/1966 | Martin et al. | | 3,517,553 A | 6/1970 | Williams et al. |
| 3,260,091 A | 7/1966 | Shaw, Jr. | | 3,527,226 A | 9/1970 | Hakin et al. |
| 3,265,822 A | 8/1966 | Moulten | | 3,529,908 A | 9/1970 | Smith |
| 3,266,487 A | 8/1966 | Watkins et al. | | 3,530,449 A | 9/1970 | Anderson |
| 3,273,447 A | 9/1966 | Frank | | 3,533,403 A | 10/1970 | Woodson |
| 3,283,352 A | 11/1966 | Hu | | 3,534,728 A | 10/1970 | Barrows |
| 3,290,919 A | 12/1966 | Malinak et al. | | 3,534,872 A | 10/1970 | Roth et al. |
| 3,292,493 A | 12/1966 | Franklin | | 3,535,914 A | 10/1970 | Veith et al. |
| 3,292,888 A | 12/1966 | Fischer | | 3,539,009 A | 11/1970 | Kudlaty |
| 3,294,988 A | 12/1966 | Packard | | 3,543,744 A | 12/1970 | LePar |
| 3,299,603 A | 1/1967 | Shaw | | 3,545,275 A | 12/1970 | Harrison et al. |
| 3,299,882 A | 1/1967 | Masino | | 3,550,583 A | 12/1970 | Chiku |
| 3,301,514 A | 1/1967 | Sugaya | | 3,550,847 A | 12/1970 | Scott |
| 3,302,457 A | 2/1967 | Mayes | | 3,563,094 A | 2/1971 | Rieschel |
| 3,306,384 A | 2/1967 | Ross | | 3,563,245 A | 2/1971 | McLean et al. |
| 3,313,314 A | 4/1967 | Burke et al. | | 3,566,083 A | 2/1971 | McMillin |
| 3,316,935 A | 5/1967 | Kaiser et al. | | 3,566,875 A | 3/1971 | Stoehr |
| 3,320,750 A | 5/1967 | Haise et al. | | 3,568,367 A | 3/1971 | Myers |
| 3,321,035 A | 5/1967 | Tarpley | | 3,568,636 A | 3/1971 | Lockwood |
| 3,332,788 A | 7/1967 | Barnby | | 3,576,554 A | 4/1971 | Temps, Jr. et al. |
| 3,334,510 A | 8/1967 | Hallesy | | 3,580,082 A | 5/1971 | Strack |
| 3,339,401 A | 9/1967 | Peters | | 3,581,402 A | 6/1971 | London et al. |
| 3,340,868 A | 9/1967 | Darling | | 3,583,387 A | 6/1971 | Garner et al. |
| 3,347,162 A | 10/1967 | Braznell | | 3,587,204 A | 6/1971 | George |
| 3,350,944 A | 11/1967 | De Michele | | 3,590,809 A | 7/1971 | London |
| 3,353,364 A | 11/1967 | Blanding et al. | | 3,590,818 A | 7/1971 | Lemole |
| 3,353,481 A | 11/1967 | Antonucci | | 3,590,992 A | 7/1971 | Soderstrom et al. |
| 3,356,334 A | 12/1967 | Scaramucci | | 3,592,183 A | 7/1971 | Watkins et al. |
| 3,356,510 A | 12/1967 | Barnby | | 3,594,519 A | 7/1971 | Schmidlin |
| 3,357,218 A | 12/1967 | Mitchell | | 3,602,885 A | 8/1971 | Grajeda |
| 3,357,461 A | 12/1967 | Friendship | | 3,610,016 A | 10/1971 | Bultman |
| 3,359,741 A | 12/1967 | Nelson | | 3,610,851 A | 10/1971 | Krupski |
| 3,361,300 A | 1/1968 | Kaplan | | 3,611,811 A | 10/1971 | Lissau |
| 3,364,929 A | 1/1968 | Ide et al. | | 3,614,926 A | 10/1971 | Brechtel |
| 3,365,684 A | 1/1968 | Stemke | | 3,614,955 A | 10/1971 | Mirowski et al. |
| 3,378,456 A | 4/1968 | Roberts | | 3,619,742 A | 11/1971 | Rud, Jr. |
| 3,380,445 A | 4/1968 | Frasier | | 3,623,371 A | 11/1971 | Jullien-Davin |
| 3,380,649 A | 4/1968 | Roberts | | 3,624,854 A | 12/1971 | Strong |
| 3,385,022 A | 5/1968 | Anderson | | 3,630,242 A | 12/1971 | Schieser et al. |
| 3,389,355 A | 6/1968 | Schroeder, Jr. | | 3,631,847 A | 1/1972 | Hobbs, II |
| 3,393,612 A | 7/1968 | Gorgens et al. | | 3,633,881 A | 1/1972 | Yurdin |
| 3,396,561 A | 8/1968 | Day | | 3,635,061 A | 1/1972 | Rydell et al. |
| 3,399,667 A | 9/1968 | Nishimoto et al. | | 3,635,074 A | 1/1972 | Moos et al. |
| 3,400,734 A | 9/1968 | Rosenberg | | 3,638,496 A | 2/1972 | King |
| 3,403,237 A | 9/1968 | Wysong | | 3,644,883 A | 2/1972 | Borman et al. |
| 3,409,924 A | 11/1968 | Slama | | 3,648,687 A | 3/1972 | Ramsey, III |
| 3,411,347 A | 11/1968 | Wirth et al | | 3,651,289 A | 3/1972 | Nagashima et al. |
| 3,417,476 A | 12/1968 | Martens | | 3,651,405 A | 3/1972 | Whitney et al. |
| 3,420,325 A | 1/1969 | McAlister et al. | | 3,653,671 A | 4/1972 | Shipes |
| 3,422,324 A | 1/1969 | Webb | | 3,659,615 A | 5/1972 | Enger |
| 3,426,165 A | 2/1969 | Beaman | | 3,677,685 A | 7/1972 | Aoki et al. |
| 3,438,391 A | 4/1969 | Yocum | | 3,686,958 A | 8/1972 | Porter et al. |
| 3,443,608 A | 5/1969 | Copping et al. | | 3,688,568 A | 9/1972 | Karper at al. |
| 3,445,335 A | 5/1969 | Gluntz | | 3,701,392 A | 10/1972 | Wirth et al. |
| 3,447,281 A | 6/1969 | Bufford et al. | | 3,702,677 A | 11/1972 | Heffington |
| 3,450,153 A | 6/1969 | Hildebrandt et al. | | 3,703,099 A | 11/1972 | Rouse et al. |
| 3,453,546 A | 7/1969 | Fryer | | 3,712,138 A | 1/1973 | Alinari et al. |
| 3,453,848 A | 7/1969 | Williamson | | 3,713,124 A | 1/1973 | Durland et al. |
| 3,456,134 A | 7/1969 | Ko | | 3,719,524 A | 3/1973 | Ripley at al. |
| 3,457,909 A | 7/1969 | Laird | | 3,721,412 A | 3/1973 | Kindorf |
| 3,460,557 A | 8/1969 | Gallant | | 3,723,247 A | 3/1973 | Leine at al. |
| 3,463,338 A | 8/1969 | Schnerider | | 3,724,000 A | 4/1973 | Eakman |
| 3,469,818 A | 9/1969 | Cowan | | 3,727,463 A | 4/1973 | Intraub |
| 3,470,725 A | 10/1969 | Brown et al. | | 3,727,616 A | 4/1973 | Lenzkes |
| 3,472,230 A | 10/1969 | Fogarty | | 3,730,174 A | 5/1973 | Madison |
| 3,478,344 A | 11/1969 | Schwitzgebel et al. | | 3,730,560 A | 5/1973 | Abildgaard et al. |
| 3,482,449 A | 12/1969 | Werner | | 3,731,679 A | 5/1973 | Wilhelmson et al. |
| 3,482,816 A | 12/1969 | Arnold | | 3,731,681 A | 5/1973 | Blackshear et al. |
| 3,487,959 A | 1/1970 | Pearne et al. | | 3,732,731 A | 5/1973 | Fussell, Jr. |
| 3,491,842 A | 1/1970 | Delacour et al. | | 3,735,040 A | 5/1973 | Punt et al. |
| 3,492,638 A | 1/1970 | Lane | | 3,736,930 A | 6/1973 | Georgi |
| 3,502,829 A | 3/1970 | Reynolds | | 3,738,356 A | 6/1973 | Workman |
| 3,503,116 A | 3/1970 | Strack | | 3,740,921 A | 6/1973 | Meyer et al. |
| 3,504,664 A | 4/1970 | Haddad | | 3,746,111 A | 7/1973 | Berthiaume et al. |
| 3,505,808 A | 4/1970 | Eschle | | 3,748,678 A | 7/1973 | Ballou |
| 3,509,754 A | 5/1970 | Massingill et al. | | 3,749,098 A | 7/1973 | De Bennetot et al. |

| Patent | Date | Inventor |
|---|---|---|
| 3,749,422 A | 7/1973 | Abildgaard et al. |
| 3,749,423 A | 7/1973 | Abildgaard et al. |
| 3,750,194 A | 8/1973 | Summers |
| 3,757,770 A | 9/1973 | Brayshaw et al. |
| 3,759,095 A | 9/1973 | Short, Jr. et al. |
| 3,760,638 A | 9/1973 | Lawson et al. |
| 3,763,960 A | 10/1973 | John et al. |
| 3,765,142 A | 10/1973 | Lindquist et al. |
| 3,765,494 A | 10/1973 | Kielman, Jr. |
| 3,769,156 A | 10/1973 | Brecy et al. |
| 3,769,830 A | 11/1973 | Porter et al. |
| 3,774,243 A | 11/1973 | Ng et al. |
| 3,776,333 A | 12/1973 | Mathauser |
| 3,778,051 A | 12/1973 | Allen et al. |
| 3,780,578 A | 12/1973 | Sellman et al. |
| 3,781,902 A | 12/1973 | Shim et al. |
| 3,783,585 A | 1/1974 | Hoyland et al. |
| 3,789,667 A | 2/1974 | Porter et al. |
| 3,796,095 A | 3/1974 | Fussell, Jr. |
| 3,807,219 A | 4/1974 | Wallskog |
| 3,811,429 A | 5/1974 | Fletcher et al. |
| 3,815,722 A | 6/1974 | Sessoms |
| 3,818,765 A | 6/1974 | Eriksen et al. |
| 3,820,400 A | 6/1974 | Russo |
| 3,820,795 A | 6/1974 | Taylor |
| 3,823,610 A | 7/1974 | Fussell, Jr. |
| 3,825,065 A | 7/1974 | Lloyd et al. |
| 3,825,963 A | 7/1974 | Abildgaard et al. |
| 3,825,964 A | 7/1974 | Groswith, III et al. |
| 3,828,672 A | 8/1974 | Gazzola et al. |
| 3,828,766 A | 8/1974 | Krasnow |
| 3,831,588 A | 8/1974 | Rindner |
| 3,831,942 A | 8/1974 | Del Mar |
| 3,833,238 A | 9/1974 | Liard et al. |
| 3,834,167 A | 9/1974 | Tabor |
| 3,834,739 A | 9/1974 | Abildgaard et al. |
| 3,835,523 A | 9/1974 | Stansfield et al. |
| 3,839,708 A | 10/1974 | Bredesen et al. |
| 3,842,483 A | 10/1974 | Cramer |
| 3,842,668 A | 10/1974 | Lippke et al. |
| 3,845,664 A | 11/1974 | Perry, Jr. |
| 3,845,751 A | 11/1974 | Runstetler |
| 3,845,757 A | 11/1974 | Weyer |
| 3,847,434 A | 11/1974 | Weman et al. |
| 3,850,208 A | 11/1974 | Hamilton |
| 3,853,117 A | 12/1974 | Murr |
| 3,854,469 A | 12/1974 | Giori et al. |
| 3,855,902 A | 12/1974 | Kirst et al. |
| 3,857,399 A | 12/1974 | Zacouto et al. |
| 3,857,452 A | 12/1974 | Hartman |
| 3,857,745 A | 12/1974 | Grausch et al. |
| 3,858,581 A | 1/1975 | Kamen |
| 3,863,622 A | 2/1975 | Buuck |
| 3,863,933 A | 2/1975 | Tredway |
| 3,867,950 A | 2/1975 | Fischell |
| 3,868,008 A | 2/1975 | Brumbaugh |
| 3,868,679 A | 2/1975 | Arneson |
| 3,871,599 A | 3/1975 | Takada et al. |
| 3,872,285 A | 3/1975 | Shum et al. |
| 3,874,388 A | 4/1975 | King et al. |
| 3,876,980 A | 4/1975 | Haemmig et al. |
| 3,878,908 A | 4/1975 | Andersson et al. |
| 3,881,528 A | 5/1975 | Mackenzie |
| 3,893,111 A | 7/1975 | Cotter |
| 3,893,451 A | 7/1975 | Durand et al. |
| 3,895,681 A | 7/1975 | Griffin et al. |
| 3,899,862 A | 8/1975 | Muys et al. |
| 3,904,234 A | 9/1975 | Hill et al. |
| 3,908,334 A | 9/1975 | Rychiger et al. |
| 3,908,461 A | 9/1975 | Turpen |
| 3,908,721 A | 9/1975 | McGahey et al. |
| 3,910,087 A | 10/1975 | Jones |
| 3,912,168 A | 10/1975 | Mullins et al. |
| 3,912,304 A | 10/1975 | Abildgaard et al. |
| 3,918,286 A | 11/1975 | Whitehead |
| 3,918,291 A | 11/1975 | Pauly et al. |
| 3,920,965 A | 11/1975 | Sohrwardy et al. |
| 3,921,682 A | 11/1975 | McGahey et al. |
| 3,922,951 A | 12/1975 | Linsinger et al. |
| 3,923,060 A | 12/1975 | Ellinwood, Jr. |
| 3,924,635 A | 12/1975 | Hakim et al. |
| 3,928,980 A | 12/1975 | Ganzinotti et al. |
| 3,929,175 A | 12/1975 | Coone |
| 3,930,682 A | 1/1976 | Booth |
| 3,930,852 A | 1/1976 | Tanaka et al. |
| 3,936,028 A | 2/1976 | Norton et al. |
| 3,940,122 A | 2/1976 | Janzen et al. |
| 3,940,630 A | 2/1976 | Bergonz |
| 3,942,299 A | 3/1976 | Bory et al. |
| 3,942,382 A | 3/1976 | Hok et al. |
| 3,942,516 A | 3/1976 | Glynn et al. |
| 3,942,536 A | 3/1976 | Mirowski et al. |
| 3,943,915 A | 3/1976 | Severson |
| 3,945,704 A | 3/1976 | Kraus et al. |
| 3,946,613 A | 3/1976 | Silver |
| 3,946,615 A | 3/1976 | Hluchan |
| 3,946,724 A | 3/1976 | La Balme et al. |
| 3,948,141 A | 4/1976 | Shinjo et al. |
| 3,949,388 A | 4/1976 | Fuller |
| 3,953,289 A | 4/1976 | Costes et al. |
| 3,954,271 A | 5/1976 | Tredway, Sr. |
| 3,958,558 A | 5/1976 | Dunphy et al. |
| 3,961,425 A | 6/1976 | Swanson et al. |
| 3,961,646 A | 6/1976 | Schon et al. |
| 3,962,895 A | 6/1976 | Rydell et al. |
| 3,962,921 A | 6/1976 | Lips |
| 3,963,019 A | 6/1976 | Quandt |
| 3,964,485 A | 6/1976 | Neumeier |
| 3,964,770 A | 6/1976 | Abildgaard et al. |
| 3,967,737 A | 7/1976 | Peralta et al. |
| 3,968,473 A | 7/1976 | Patton et al. |
| 3,968,694 A | 7/1976 | Clark |
| 3,972,320 A | 8/1976 | Kalman |
| 3,973,753 A | 8/1976 | Wheeler |
| 3,973,858 A | 8/1976 | Poisson et al. |
| 3,974,655 A | 8/1976 | Halpern et al. |
| 3,974,865 A | 8/1976 | Fenton et al. |
| 3,977,391 A | 8/1976 | Fleischmann |
| 3,980,871 A | 9/1976 | Lindstrom et al. |
| 3,982,571 A | 9/1976 | Fenton et al. |
| 3,983,948 A | 10/1976 | Jeter |
| 3,985,133 A | 10/1976 | Jenkins et al. |
| 3,987,860 A | 10/1976 | Jabsen |
| 3,989,005 A | 11/1976 | Bowler, Jr. et al. |
| 3,991,749 A | 11/1976 | Zent |
| 3,992,948 A | 11/1976 | D'Antonio et al. |
| 3,993,149 A | 11/1976 | Harvey |
| 3,996,927 A | 12/1976 | Frank |
| 3,996,962 A | 12/1976 | Sutherland |
| 4,003,141 A | 1/1977 | Le Roy |
| 4,005,282 A | 1/1977 | Jennings |
| 4,005,593 A | 2/1977 | Goldberg |
| 4,006,735 A | 2/1977 | Hittman et al. |
| 4,009,375 A | 2/1977 | White et al. |
| 4,009,591 A | 3/1977 | Hester |
| 4,010,449 A | 3/1977 | Faggin et al. |
| 4,014,319 A | 3/1977 | Favre et al. |
| 4,014,321 A | 3/1977 | March |
| 4,016,764 A | 4/1977 | Rice |
| 4,017,329 A | 4/1977 | Larson |
| 4,018,134 A | 4/1977 | Linsinger et al. |
| 4,022,190 A | 5/1977 | Meyer |
| 4,024,864 A | 5/1977 | Davies et al. |
| 4,025,912 A | 5/1977 | Rice |
| 4,026,276 A | 5/1977 | Chubbuck |
| 4,027,661 A | 6/1977 | Lyon et al. |
| 4,031,899 A | 6/1977 | Renirie et al. |
| 4,036,775 A | 7/1977 | Trautvetter et al. |
| 4,039,069 A | 8/1977 | Kwan et al. |
| 4,041,954 A | 8/1977 | Ohara et al. |
| 4,042,504 A | 8/1977 | Drori et al. |
| 4,045,345 A | 8/1977 | Drori et al. |
| 4,047,851 A | 9/1977 | Bender |
| 4,048,494 A | 9/1977 | Liesting et al. |
| 4,048,879 A | 9/1977 | Cox |
| 4,049,004 A | 9/1977 | Walters |
| 4,051,338 A | 9/1977 | Harris, III |
| 4,052,991 A | 10/1977 | Zacouto et al. |

| | | | | | |
|---|---|---|---|---|---|
| 4,055,074 A | 10/1977 | Thimons et al. | 4,191,004 A | 3/1980 | Gmuer et al. |
| 4,055,175 A | 10/1977 | Clemens et al. | 4,191,187 A | 3/1980 | Wright et al. |
| 4,056,854 A | 11/1977 | Boretos et al. | 4,192,192 A | 3/1980 | Schnell |
| 4,058,007 A | 11/1977 | Exner et al. | 4,193,397 A | 3/1980 | Tucker et al. |
| 4,062,351 A | 12/1977 | Hastwell et al. | 4,204,547 A | 5/1980 | Allocca |
| 4,062,354 A | 12/1977 | Taylor et al. | 4,206,755 A | 6/1980 | Klein et al. |
| 4,062,360 A | 12/1977 | Bentley | 4,206,761 A | 6/1980 | Cosman |
| 4,063,439 A | 12/1977 | Besson et al. | 4,206,762 A | 6/1980 | Cosman |
| 4,064,882 A | 12/1977 | Johnson et al. | 4,207,903 A | 6/1980 | O'Neill |
| 4,070,239 A | 1/1978 | Bevilacqua | 4,212,074 A | 7/1980 | Kuno et al. |
| 4,072,047 A | 2/1978 | Reismuller et al. | 4,217,221 A | 8/1980 | Masso |
| 4,073,292 A | 2/1978 | Edelman | 4,217,588 A | 8/1980 | Freeny, Jr. |
| 4,075,099 A | 2/1978 | Pelton et al. | 4,220,189 A | 9/1980 | Marquez |
| 4,075,602 A | 2/1978 | Clothier | 4,221,219 A | 9/1980 | Tucker |
| 4,077,072 A | 3/1978 | Dezura et al. | 4,221,523 A | 9/1980 | Eberle |
| 4,077,394 A | 3/1978 | McCurdy | 4,222,377 A | 9/1980 | Burton |
| 4,077,405 A | 3/1978 | Haerten et al. | 4,223,837 A | 9/1980 | Gubbiotti et al. |
| 4,077,882 A | 3/1978 | Gangemi | 4,226,124 A | 10/1980 | Kersten et al. |
| 4,078,620 A | 3/1978 | Westlake et al. | 4,226,229 A | 10/1980 | Eckhart et al. |
| 4,080,653 A | 3/1978 | Barnes, Jr. et al. | 4,227,533 A | 10/1980 | Godfrey |
| 4,084,752 A | 4/1978 | Hagiwara et al. | 4,231,376 A | 11/1980 | Lyon et al. |
| 4,086,488 A | 4/1978 | Hill | 4,232,682 A | 11/1980 | Veth |
| 4,087,568 A | 5/1978 | Fay et al. | 4,237,900 A | 12/1980 | Schulman et al. |
| 4,088,417 A | 5/1978 | Kosmowski | 4,241,247 A | 12/1980 | Byrne et al. |
| 4,089,329 A | 5/1978 | Couvillon, Jr. et al. | 4,241,870 A | 12/1980 | Marcus |
| 4,090,802 A | 5/1978 | Bilz et al. | 4,245,593 A | 1/1981 | Stein |
| 4,092,719 A | 5/1978 | Salmon et al. | 4,246,877 A | 1/1981 | Kennedy |
| 4,092,925 A | 6/1978 | Fromson | 4,247,850 A | 1/1981 | Marcus |
| 4,096,866 A | 6/1978 | Fischell | 4,248,238 A | 2/1981 | Joseph et al. |
| 4,098,293 A | 7/1978 | Kramer et al. | 4,248,241 A | 2/1981 | Tacchi |
| 4,103,496 A | 8/1978 | Colamussi et al. | 4,256,094 A | 3/1981 | Kapp et al. |
| 4,106,370 A | 8/1978 | Kraus et al. | 4,256,118 A | 3/1981 | Nagel et al. |
| 4,107,689 A | 8/1978 | Jellinek | 4,262,343 A | 4/1981 | Claycomb |
| 4,107,995 A | 8/1978 | Ligman et al. | 4,262,632 A | 4/1981 | Hanton et al. |
| 4,108,148 A | 8/1978 | Cannon, III | 4,265,241 A | 5/1981 | Portner et al. |
| 4,108,575 A | 8/1978 | Schal et al. | 4,265,252 A | 5/1981 | Chubbuck et al. |
| 4,109,148 A | 8/1978 | Jaulmes et al. | 4,271,018 A | 6/1981 | Drori et al. |
| 4,109,518 A | 8/1978 | Dooley et al. | 4,273,070 A | 6/1981 | Hoefelmayr et al. |
| 4,109,644 A | 8/1978 | Kojima | 4,274,444 A | 6/1981 | Ruyak |
| 4,111,056 A | 9/1978 | Mastromatteo | 4,275,600 A | 6/1981 | Turner et al. |
| 4,111,629 A | 9/1978 | Nussbaumer et al. | 4,275,913 A | 6/1981 | Marcus |
| 4,114,424 A | 9/1978 | Johnson | 4,278,540 A | 7/1981 | Drori et al. |
| 4,114,606 A | 9/1978 | Seylar | 4,280,036 A | 7/1981 | Fukatsu et al. |
| 4,120,097 A | 10/1978 | Jeter | 4,280,775 A | 7/1981 | Wood |
| 4,120,134 A | 10/1978 | Scholle | 4,281,666 A | 8/1981 | Cosman |
| 4,121,635 A | 10/1978 | Hansel | 4,281,667 A | 8/1981 | Cosman |
| 4,123,310 A | 10/1978 | Varon et al. | 4,284,073 A | 8/1981 | Krause et al. |
| 4,124,023 A | 11/1978 | Fleischmann et al. | 4,285,770 A | 8/1981 | Chi et al. |
| 4,127,110 A | 11/1978 | Bullara | 4,291,699 A | 9/1981 | Geddes et al. |
| 4,130,169 A | 12/1978 | Denison | 4,295,963 A | 10/1981 | Drori et al. |
| 4,131,596 A | 12/1978 | Allen | 4,297,927 A | 11/1981 | Kuroda et al. |
| 4,133,355 A | 1/1979 | Mayer | 4,303,075 A | 12/1981 | Heilman et al. |
| 4,133,367 A | 1/1979 | Abell | 4,305,402 A | 12/1981 | Katims |
| 4,140,131 A | 2/1979 | Dutcher et al. | 4,312,374 A | 1/1982 | Drori et al. |
| 4,141,348 A | 2/1979 | Hittman | 4,314,480 A | 2/1982 | Becker |
| 4,141,349 A | 2/1979 | Ory et al. | 4,316,693 A | 2/1982 | Baxter et al. |
| 4,143,661 A | 3/1979 | LaForge et al. | 4,325,387 A | 4/1982 | Helfer |
| 4,146,029 A | 3/1979 | Ellinwood, Jr. | 4,327,804 A | 5/1982 | Reed |
| 4,147,161 A | 4/1979 | Ikebe et al. | 4,328,654 A | 5/1982 | Van Ginkel et al. |
| 4,148,096 A | 4/1979 | Haas et al. | 4,332,254 A | 6/1982 | Lundquist |
| 4,149,423 A | 4/1979 | Frosch et al. | 4,339,831 A | 7/1982 | Johnson |
| 4,151,823 A | 5/1979 | Grosse et al. | 4,342,218 A | 8/1982 | Fox |
| 4,153,085 A | 5/1979 | Adams | 4,342,308 A | 8/1982 | Trick |
| 4,156,422 A | 5/1979 | Hildebrandt et al. | 4,346,604 A | 8/1982 | Snook et al. |
| 4,160,448 A | 7/1979 | Jackson | 4,347,851 A | 9/1982 | Jundanian |
| 4,160,971 A | 7/1979 | Jones et al. | 4,350,647 A | 9/1982 | de la Cruz |
| 4,166,469 A | 9/1979 | Littleford | 4,350,970 A | 9/1982 | von Tomkewitsch et al. |
| 4,167,304 A | 9/1979 | Gelbke | 4,351,037 A | 9/1982 | Scherbatskoy |
| 4,167,952 A | 9/1979 | Reinicke | 4,351,116 A | 9/1982 | Scott, Jr. |
| 4,168,567 A | 9/1979 | Leguy et al. | 4,356,486 A | 10/1982 | Mount |
| 4,170,280 A | 10/1979 | Schwarz | 4,360,010 A | 11/1982 | Finney |
| 4,171,218 A | 10/1979 | Hoshino et al. | 4,360,277 A | 11/1982 | Daniel et al. |
| 4,183,124 A | 1/1980 | Hoffman | 4,361,153 A | 11/1982 | Slocum et al. |
| 4,183,247 A | 1/1980 | Allen et al. | 4,363,236 A | 12/1982 | Meyers |
| 4,185,641 A | 1/1980 | Minior et al. | 4,364,276 A | 12/1982 | Shimazoe et al. |
| 4,186,287 A | 1/1980 | Scott | 4,365,425 A | 12/1982 | Gotchel |
| 4,186,749 A | 2/1980 | Fryer | 4,368,937 A | 1/1983 | Palombo et al. |
| 4,186,751 A | 2/1980 | Fleischmann | 4,369,013 A | 1/1983 | Abildgaard et al. |
| 4,190,057 A | 2/1980 | Hill et al. | 4,373,527 A | 2/1983 | Fischell |

| | | | | | | |
|---|---|---|---|---|---|---|
| 4,376,523 A | 3/1983 | Goyen et al. | | 4,499,750 A | 2/1985 | Gerber et al. |
| 4,378,809 A | 4/1983 | Cosman | | 4,503,678 A | 3/1985 | Wimbush et al. |
| 4,380,427 A | 4/1983 | Hehl et al. | | 4,511,974 A | 4/1985 | Nakane et al. |
| 4,385,636 A | 5/1983 | Cosman | | 4,513,295 A | 4/1985 | Jones et al. |
| 4,386,422 A | 5/1983 | Mumby et al. | | 4,515,004 A | 5/1985 | Jaenson |
| 4,387,907 A | 6/1983 | Hiestand et al. | | 4,515,750 A | 5/1985 | Pardini et al. |
| 4,392,368 A | 7/1983 | Folkesson et al. | | 4,516,866 A | 5/1985 | Yamauchi et al. |
| 4,393,899 A | 7/1983 | Tsuji et al. | | 4,518,637 A | 5/1985 | Takeda et al. |
| 4,393,951 A | 7/1983 | Horst-Rudolf et al. | | 4,519,401 A | 5/1985 | Ko et al. |
| 4,395,232 A | 7/1983 | Koch | | 4,520,443 A | 5/1985 | Yuki et al. |
| 4,395,258 A | 7/1983 | Wang et al. | | 4,522,213 A | 6/1985 | Wallroth et al. |
| 4,395,916 A | 8/1983 | Martin | | 4,527,568 A | 7/1985 | Rickards et al. |
| 4,398,983 A | 8/1983 | Suzuki et al. | | 4,529,401 A | 7/1985 | Leslie et al. |
| 4,399,705 A | 8/1983 | Weiger et al. | | 4,531,526 A | 7/1985 | Genest |
| 4,399,707 A | 8/1983 | Wamstad | | 4,531,936 A | 7/1985 | Gordon |
| 4,399,809 A | 8/1983 | Baro et al. | | 4,536,000 A | 8/1985 | Rohm et al. |
| 4,399,821 A | 8/1983 | Bowers | | 4,537,005 A | 8/1985 | Hoyland et al. |
| 4,403,984 A | 9/1983 | Ash et al. | | 4,537,129 A | 8/1985 | Heinemann et al. |
| 4,404,968 A | 9/1983 | Evans, Sr. | | 4,538,616 A | 9/1985 | Rogoff |
| 4,404,974 A | 9/1983 | Titus | | 4,540,404 A | 9/1985 | Wolvek |
| 4,405,318 A | 9/1983 | Whitney et al. | | 4,542,461 A | 9/1985 | Eldridge et al. |
| 4,407,125 A | 10/1983 | Parsons et al. | | 4,544,369 A | 10/1985 | Skakoon et al. |
| 4,407,271 A | 10/1983 | Schiff | | 4,545,185 A | 10/1985 | Chikatani et al. |
| 4,407,296 A | 10/1983 | Anderson | | 4,546,524 A | 10/1985 | Kreft |
| 4,407,326 A | 10/1983 | Wilhelm | | 4,548,209 A | 10/1985 | Wielders et al. |
| 4,408,597 A | 10/1983 | Tenney, Jr. | | 4,552,150 A | 11/1985 | Zacouto et al. |
| 4,408,615 A | 10/1983 | Grossman | | 4,553,226 A | 11/1985 | Scherbatskoy |
| 4,415,071 A | 11/1983 | Butler et al. | | 4,556,063 A | 12/1985 | Thompson et al. |
| 4,416,282 A | 11/1983 | Saulson et al. | | 4,557,269 A | 12/1985 | Reynolds et al. |
| 4,418,899 A | 12/1983 | Zimmermann et al. | | 4,557,332 A | 12/1985 | Denison et al. |
| 4,419,393 A | 12/1983 | Hanson et al. | | 4,559,815 A | 12/1985 | Needham et al. |
| 4,421,505 A | 12/1983 | Schwartz | | 4,560,979 A | 12/1985 | Rosskopf et al. |
| 4,424,720 A | 1/1984 | Bucchianeri | | 4,561,442 A | 12/1985 | Vollmann et al. |
| 4,428,228 A | 1/1984 | Banzhaf et al. | | 4,562,751 A | 1/1986 | Nason et al. |
| 4,428,365 A | 1/1984 | Hakky et al. | | 4,563,175 A | 1/1986 | LaFond |
| 4,430,899 A | 2/1984 | Wessel et al. | | 4,565,116 A | 1/1986 | Hehl et al. |
| 4,431,009 A | 2/1984 | Marino, Jr. et al. | | 4,566,456 A | 1/1986 | Koning et al. |
| 4,431,365 A | 2/1984 | Sturtz, Jr. | | 4,569,623 A | 2/1986 | Goldmann |
| 4,432,363 A | 2/1984 | Kakegawa et al. | | 4,570,351 A | 2/1986 | Szanto et al. |
| 4,435,173 A | 3/1984 | Siposs et al. | | 4,571,161 A | 2/1986 | Leblanc et al. |
| 4,439,186 A | 3/1984 | Kuhl et al. | | 4,571,995 A | 2/1986 | Timme |
| 4,441,491 A | 4/1984 | Evans, Sr. | | 4,573,835 A | 3/1986 | Eckardt et al. |
| 4,441,501 A | 4/1984 | Parent | | 4,574,792 A | 3/1986 | Trick |
| 4,444,194 A | 4/1984 | Burcham | | 4,576,181 A | 3/1986 | Wallace et al. |
| 4,444,498 A | 4/1984 | Heinemann | | 4,576,183 A | 3/1986 | Plicchi et al. |
| 4,445,385 A | 5/1984 | Endo | | 4,577,512 A | 3/1986 | Lowenheck et al. |
| 4,446,711 A | 5/1984 | Valente | | 4,581,018 A | 4/1986 | Jassawalla et al. |
| 4,447,224 A | 5/1984 | DeCant, Jr. et al. | | 4,581,915 A | 4/1986 | Haulsee et al. |
| 4,449,493 A | 5/1984 | Kopec et al. | | 4,587,840 A | 5/1986 | Dobler et al. |
| 4,450,811 A | 5/1984 | Ichikawa et al. | | 4,589,805 A | 5/1986 | Duffner et al. |
| 4,451,033 A | 5/1984 | Nestegard | | 4,592,339 A | 6/1986 | Kuzmak et al. |
| 4,453,537 A | 6/1984 | Spitzer | | 4,592,340 A | 6/1986 | Boyles |
| 4,453,578 A | 6/1984 | Wilder | | 4,593,703 A | 6/1986 | Cosman |
| 4,460,835 A | 7/1984 | Masuoka et al. | | 4,595,228 A | 6/1986 | Chu |
| 4,464,170 A | 8/1984 | Clemens et al. | | 4,596,563 A | 6/1986 | Pande |
| 4,465,015 A | 8/1984 | Osta et al. | | 4,599,943 A | 7/1986 | Kobler et al. |
| 4,465,474 A | 8/1984 | Mardorf et al. | | 4,600,855 A | 7/1986 | Strachan et al. |
| 4,466,290 A | 8/1984 | Frick | | 4,602,541 A | 7/1986 | Benzinger et al. |
| 4,468,172 A | 8/1984 | Dixon et al. | | 4,604,089 A | 8/1986 | Santangelo et al. |
| 4,468,762 A | 8/1984 | Jurgens et al. | | 4,605,354 A | 8/1986 | Daly |
| 4,469,365 A | 9/1984 | Marcus et al. | | 4,606,419 A | 8/1986 | Perini |
| 4,471,182 A | 9/1984 | Wielgos et al. | | 4,606,478 A | 8/1986 | Hack et al. |
| 4,471,786 A | 9/1984 | Inagaki et al. | | 4,610,256 A | 9/1986 | Wallace |
| 4,473,067 A | 9/1984 | Schiff | | 4,614,137 A | 9/1986 | Jones |
| 4,473,078 A | 9/1984 | Angel | | 4,617,016 A | 10/1986 | Blomberg et al. |
| 4,476,721 A | 10/1984 | Hochreuther et al. | | 4,618,861 A | 10/1986 | Gettens et al. |
| 4,478,213 A | 10/1984 | Redding | | 4,620,807 A | 11/1986 | Polit |
| 4,478,538 A | 10/1984 | Kakino et al. | | 4,621,331 A | 11/1986 | Iwata et al. |
| 4,483,196 A | 11/1984 | Kurtz et al. | | 4,622,871 A | 11/1986 | Van Sickle et al. |
| 4,484,135 A | 11/1984 | Ishihara et al. | | 4,626,462 A | 12/1986 | Kober et al. |
| 4,485,813 A | 12/1984 | Anderson et al. | | 4,633,304 A | 12/1986 | Nagasaki et al. |
| 4,489,916 A | 12/1984 | Stevens | | 4,633,878 A | 1/1987 | Bombardieri et al. |
| 4,492,632 A | 1/1985 | Mattson | | 4,634,427 A * | 1/1987 | Hannula et al. ......... 604/288.02 |
| 4,494,411 A | 1/1985 | Koschke et al. | | 4,635,182 A | 1/1987 | Hintz |
| 4,494,950 A | 1/1985 | Fischell | | 4,637,736 A | 1/1987 | Andeen et al. |
| 4,497,176 A | 2/1985 | Rubin et al. | | 4,638,665 A | 1/1987 | Benson et al. |
| 4,497,201 A | 2/1985 | Allen et al. | | 4,644,246 A | 2/1987 | Knapen et al. |
| 4,499,394 A | 2/1985 | Koal | | 4,646,553 A | 3/1987 | Tufte et al. |
| 4,499,691 A | 2/1985 | Karazim et al. | | 4,648,363 A | 3/1987 | Kronich |

| | | | | | | |
|---|---|---|---|---|---|---|
| 4,648,406 A | 3/1987 | Miller | | 4,803,987 A | 2/1989 | Calfee et al. |
| 4,658,358 A | 4/1987 | Leach et al. | | 4,804,368 A | 2/1989 | Skakoon et al. |
| 4,658,760 A | 4/1987 | Zebuhr | | 4,807,321 A | 2/1989 | Grasselli et al. |
| 4,660,568 A | 4/1987 | Cosman | | 4,808,167 A | 2/1989 | Mann et al. |
| 4,665,511 A | 5/1987 | Rodney et al. | | 4,812,823 A | 3/1989 | Dickerson |
| 4,665,896 A | 5/1987 | LaForge et al. | | 4,819,656 A | 4/1989 | Spector |
| 4,669,484 A | 6/1987 | Masters | | 4,820,265 A | 4/1989 | DeSatnick et al. |
| 4,672,974 A | 6/1987 | Lee | | 4,820,953 A | 4/1989 | Saubolle et al. |
| 4,674,457 A | 6/1987 | Berger et al. | | 4,821,167 A | 4/1989 | Wiebe |
| 4,674,546 A | 6/1987 | Fournier et al. | | 4,821,723 A | 4/1989 | Baker, Jr. et al. |
| 4,678,408 A | 7/1987 | Nason et al. | | 4,823,779 A | 4/1989 | Daly et al. |
| 4,681,559 A | 7/1987 | Hooven | | 4,830,006 A | 5/1989 | Haluska et al. |
| 4,683,850 A | 8/1987 | Bauder et al. | | 4,832,034 A | 5/1989 | Pizziconi et al. |
| 4,685,463 A | 8/1987 | Williams | | 4,833,384 A | 5/1989 | Munro et al. |
| 4,685,469 A | 8/1987 | Keller et al. | | 4,834,731 A | 5/1989 | Nowak et al. |
| 4,685,903 A | 8/1987 | Cable et al. | | 4,838,857 A | 6/1989 | Strowe et al. |
| 4,686,987 A | 8/1987 | Salo et al. | | 4,840,068 A | 6/1989 | Mayhew, Jr. |
| 4,687,530 A | 8/1987 | Berscheid et al. | | 4,840,350 A | 6/1989 | Cook et al. |
| 4,689,979 A | 9/1987 | Otsuka et al. | | 4,844,002 A | 7/1989 | Yasui et al. |
| 4,691,694 A | 9/1987 | Boyd et al. | | 4,846,153 A | 7/1989 | Berci |
| 4,691,710 A | 9/1987 | Dickens et al. | | 4,846,191 A | 7/1989 | Brockway et al. |
| 4,693,253 A | 9/1987 | Adams | | 4,846,664 A | 7/1989 | Hehl et al. |
| 4,695,237 A | 9/1987 | Inaba et al. | | 4,854,328 A | 8/1989 | Pollack |
| 4,696,189 A | 9/1987 | Hochreuther et al. | | 4,863,470 A | 9/1989 | Carter |
| 4,697,574 A | 10/1987 | Karcher et al. | | 4,865,587 A | 9/1989 | Walling |
| 4,698,038 A | 10/1987 | Key et al. | | 4,867,160 A | 9/1989 | Schaldach et al. |
| 4,700,497 A | 10/1987 | Sato et al. | | 4,867,498 A | 9/1989 | Delphia et al. |
| 4,700,610 A | 10/1987 | Bauer et al. | | 4,867,618 A | 9/1989 | Brohammer |
| 4,701,143 A | 10/1987 | Key et al. | | 4,869,252 A | 9/1989 | Gilli |
| 4,703,756 A | 11/1987 | Gough et al. | | 4,870,258 A | 9/1989 | Mochizuki et al. |
| 4,705,507 A | 11/1987 | Boyles | | 4,871,351 A | 10/1989 | Feingold et al. |
| 4,706,948 A | 11/1987 | Kroecher et al. | | 4,872,483 A | 10/1989 | Shah |
| 4,712,562 A | 12/1987 | Ohayon et al. | | 4,872,869 A | 10/1989 | Johns |
| 4,718,425 A | 1/1988 | Tanaka et al. | | 4,873,677 A | 10/1989 | Sakamoto et al. |
| 4,722,348 A | 2/1988 | Ligtenberg et al. | | 4,875,483 A | 10/1989 | Vollmann et al. |
| 4,724,806 A | 2/1988 | Hartwig et al. | | 4,880,004 A | 11/1989 | Baker, Jr. et al. |
| 4,724,830 A | 2/1988 | Fischell | | 4,882,678 A | 11/1989 | Hollis et al. |
| 4,725,826 A | 2/1988 | Hunter | | 4,886,392 A | 12/1989 | Iio et al. |
| 4,728,479 A | 3/1988 | Merkovsky | | 4,895,151 A | 1/1990 | Grevis et al. |
| 4,729,517 A | 3/1988 | Krokor et al. | | 4,896,594 A | 1/1990 | Baur et al. |
| 4,730,188 A | 3/1988 | Milheiser | | 4,898,158 A | 2/1990 | Daly et al. |
| 4,730,420 A | 3/1988 | Stratmann et al. | | 4,898,578 A | 2/1990 | Rubalcaba, Jr. |
| 4,730,619 A | 3/1988 | Koning et al. | | 4,899,751 A | 2/1990 | Cohen |
| 4,731,058 A | 3/1988 | Doan | | 4,899,752 A | 2/1990 | Cohen |
| 4,735,205 A | 4/1988 | Chachques et al. | | 4,902,277 A | 2/1990 | Mathies et al. |
| 4,738,267 A | 4/1988 | Lazorthes et al. | | 4,903,701 A | 2/1990 | Moore et al. |
| 4,738,268 A | 4/1988 | Kipnis | | 4,909,678 A | 3/1990 | Kakimoto et al. |
| 4,741,345 A | 5/1988 | Matthews et al. | | 4,913,147 A | 4/1990 | Fahlstrom et al. |
| 4,741,732 A | 5/1988 | Crankshaw et al. | | 4,919,143 A | 4/1990 | Ayers |
| 4,743,129 A | 5/1988 | Keryhuel et al. | | 4,924,872 A | 5/1990 | Frank |
| 4,745,541 A | 5/1988 | Vaniglia et al. | | 4,926,903 A | 5/1990 | Kawai et al. |
| 4,746,830 A | 5/1988 | Holland | | 4,932,406 A | 6/1990 | Berkovits |
| 4,750,495 A | 6/1988 | Moore et al. | | 4,934,369 A | 6/1990 | Maxwell |
| 4,752,115 A | 6/1988 | Murray, Jr. et al. | | 4,936,304 A | 6/1990 | Kresh et al. |
| 4,752,658 A | 6/1988 | Mack | | 4,940,037 A | 7/1990 | Eckert et al. |
| 4,757,463 A | 7/1988 | Ballou et al. | | 4,941,718 A | 7/1990 | Alexander, III et al. |
| 4,759,386 A | 7/1988 | Grouw, III | | 4,942,004 A | 7/1990 | Catanzaro |
| 4,763,649 A | 8/1988 | Merrick | | 4,944,050 A | 7/1990 | Shames et al. |
| 4,765,001 A | 8/1988 | Smith | | 4,944,298 A | 7/1990 | Sholder |
| 4,767,406 A | 8/1988 | Wadham et al. | | 4,944,307 A | 7/1990 | Hon et al. |
| 4,769,001 A | 9/1988 | Prince | | 4,945,761 A | 8/1990 | Lessi et al. |
| 4,772,896 A | 9/1988 | Nakatsu et al. | | 4,949,724 A | 8/1990 | Mahutte et al. |
| 4,773,401 A | 9/1988 | Citak et al. | | 4,952,205 A | 8/1990 | Mauerer et al. |
| 4,774,950 A | 10/1988 | Cohen | | 4,952,928 A | 8/1990 | Carroll et al. |
| 4,774,955 A | 10/1988 | Jones | | 4,953,563 A | 9/1990 | Kaiser et al. |
| 4,777,953 A | 10/1988 | Ash et al. | | 4,954,677 A | 9/1990 | Alberter et al. |
| 4,779,626 A | 10/1988 | Peel et al. | | 4,958,630 A | 9/1990 | Rosenbluth et al. |
| 4,781,192 A | 11/1988 | Demer | | 4,958,645 A | 9/1990 | Cadell et al. |
| 4,782,826 A | 11/1988 | Fogarty | | 4,960,424 A | 10/1990 | Grooters |
| 4,783,106 A | 11/1988 | Nutter | | 4,960,966 A | 10/1990 | Evans et al. |
| 4,788,847 A | 12/1988 | Sterghos | | 4,967,585 A | 11/1990 | Grimaldo |
| 4,791,318 A | 12/1988 | Lewis et al. | | 4,967,761 A | 11/1990 | Nathanielsz |
| 4,794,803 A | 1/1989 | Osterhout et al. | | 4,970,823 A | 11/1990 | Chen et al. |
| 4,796,641 A | 1/1989 | Mills et al. | | 4,971,251 A | 11/1990 | Dobrick et al. |
| 4,798,211 A | 1/1989 | Goor et al. | | 4,977,896 A | 12/1990 | Robinson et al. |
| 4,798,227 A | 1/1989 | Goodwin | | 4,978,335 A | 12/1990 | Arthur, III |
| 4,799,491 A | 1/1989 | Eckerle | | 4,978,338 A | 12/1990 | Melsky et al. |
| 4,799,625 A | 1/1989 | Weaver, Jr. et al. | | 4,979,730 A | 12/1990 | Holbrook et al. |
| 4,802,488 A | 2/1989 | Eckerle | | 4,980,671 A | 12/1990 | McCurdy |

| | | | | | |
|---|---|---|---|---|---|
| 4,981,141 A | 1/1991 | Segalowitz | 5,127,451 A | 7/1992 | Fink, Jr. et al. |
| 4,981,173 A | 1/1991 | Perkins et al. | 5,129,394 A | 7/1992 | Mehra |
| 4,981,426 A | 1/1991 | Aoki et al. | 5,129,806 A | 7/1992 | Hehl et al. |
| 4,987,897 A | 1/1991 | Funke et al. | 5,131,145 A | 7/1992 | Badoureaux et al. |
| 4,988,337 A | 1/1991 | Ito et al. | 5,131,388 A | 7/1992 | Pless et al. |
| 4,992,794 A | 2/1991 | Brouwers et al. | 5,133,358 A | 7/1992 | Gustafson et al. |
| 4,997,556 A | 3/1991 | Yano et al. | 5,135,488 A | 8/1992 | Foote et al. |
| 5,001,528 A | 3/1991 | Bahraman | 5,139,484 A | 8/1992 | Hazon et al. |
| 5,003,807 A | 4/1991 | Terrell et al. | 5,144,949 A | 9/1992 | Olson |
| 5,003,975 A | 4/1991 | Hafelfinger et al. | 5,148,580 A | 9/1992 | Dyckow et al. |
| 5,003,976 A | 4/1991 | Alt et al. | 5,148,695 A | 9/1992 | Ellis |
| 5,004,472 A | 4/1991 | Wallace | 5,152,770 A | 10/1992 | Bengmark et al. |
| 5,004,873 A | 4/1991 | Schnut | 5,152,776 A | 10/1992 | Pinchuk |
| 5,005,574 A | 4/1991 | Fearnot et al. | 5,154,170 A | 10/1992 | Bennett et al. |
| 5,005,586 A | 4/1991 | Lahr | 5,154,171 A | 10/1992 | Chirife et al. |
| 5,006,844 A | 4/1991 | Ohta et al. | 5,154,693 A | 10/1992 | East et al. |
| 5,007,401 A | 4/1991 | Grohn et al. | 5,156,972 A | 10/1992 | Issachar et al. |
| 5,007,430 A | 4/1991 | Dardik | 5,158,078 A | 10/1992 | Bennett et al. |
| 5,007,919 A | 4/1991 | Silva et al. | 5,163,429 A | 11/1992 | Cohen |
| 5,009,662 A | 4/1991 | Wallace et al. | 5,167,615 A | 12/1992 | East et al. |
| 5,010,893 A | 4/1991 | Sholder | 5,168,757 A | 12/1992 | Rabenau et al. |
| 5,012,286 A | 4/1991 | Kawano et al. | 5,168,982 A | 12/1992 | Hakanen et al. |
| 5,012,810 A | 5/1991 | Strand et al. | 5,171,299 A | 12/1992 | Heitzmann et al. |
| 5,013,292 A | 5/1991 | Lemay et al. | 5,173,873 A | 12/1992 | Wu et al. |
| 5,014,040 A | 5/1991 | Weaver et al. | 5,174,286 A | 12/1992 | Chirife et al. |
| 5,019,032 A | 5/1991 | Robertson | 5,174,291 A | 12/1992 | Schoonen et al. |
| 5,019,041 A | 5/1991 | Robinson et al. | 5,176,502 A | 1/1993 | Sanderson et al. |
| 5,020,845 A | 6/1991 | Falcoff et al. | 5,178,197 A | 1/1993 | Healy |
| 5,021,046 A | 6/1991 | Wallace | 5,181,423 A | 1/1993 | Philipps et al. |
| 5,022,395 A | 6/1991 | Russie | 5,181,517 A | 1/1993 | Hickey |
| 5,024,965 A | 6/1991 | Chang et al. | 5,184,132 A | 2/1993 | Baird |
| 5,026,180 A | 6/1991 | Tajima et al. | 5,184,614 A | 2/1993 | Collins et al. |
| 5,026,360 A | 6/1991 | Johnsen et al. | 5,184,619 A | 2/1993 | Austin |
| 5,028,918 A | 7/1991 | Giles et al. | 5,185,535 A | 2/1993 | Farb et al. |
| 5,032,822 A | 7/1991 | Sweet | 5,186,224 A | 2/1993 | Schirmacher et al. |
| 5,036,869 A | 8/1991 | Inahara et al. | 5,188,106 A | 2/1993 | Nappholz et al. |
| 5,038,800 A | 8/1991 | Oba et al. | 5,188,604 A | 2/1993 | Orth |
| 5,041,086 A | 8/1991 | Koenig et al. | 5,192,314 A | 3/1993 | Daskalakis |
| 5,041,826 A | 8/1991 | Milheiser | 5,195,362 A | 3/1993 | Eason |
| 5,042,503 A | 8/1991 | Torok et al. | 5,197,322 A | 3/1993 | Indravudh |
| 5,044,770 A | 9/1991 | Haghkar | 5,199,427 A | 4/1993 | Strickland |
| 5,046,661 A | 9/1991 | Kimura et al. | 5,199,428 A | 4/1993 | Obel et al. |
| 5,048,060 A | 9/1991 | Arai et al. | 5,201,753 A | 4/1993 | Lampropoulos et al. |
| 5,050,922 A | 9/1991 | Falcoff | 5,204,670 A | 4/1993 | Stinton |
| 5,052,910 A | 10/1991 | Hehl et al. | 5,207,429 A | 5/1993 | Walmsley et al. |
| 5,053,008 A | 10/1991 | Bajaj | 5,209,223 A | 5/1993 | McGorry et al. |
| 5,057,078 A | 10/1991 | Foote et al. | 5,209,732 A | 5/1993 | Lampropoulos et al. |
| 5,058,583 A | 10/1991 | Geddes et al. | 5,211,129 A | 5/1993 | Taylor et al. |
| 5,061,239 A | 10/1991 | Shiels | 5,211,161 A | 5/1993 | Stef et al. |
| 5,062,052 A | 10/1991 | Sparer et al. | 5,212,476 A | 5/1993 | Maloney |
| 5,062,053 A | 10/1991 | Shirai et al. | 5,213,331 A | 5/1993 | Avanzini |
| 5,062,559 A | 11/1991 | Falcoff | 5,215,523 A | 6/1993 | Williams et al. |
| 5,064,974 A | 11/1991 | Vigneau et al. | 5,218,343 A | 6/1993 | Stobbe et al. |
| 5,067,960 A | 11/1991 | Grandjean et al. | 5,218,957 A | 6/1993 | Strickland |
| 5,068,779 A | 11/1991 | Sullivan et al. | 5,226,429 A | 7/1993 | Kuzmak |
| 5,069,680 A | 12/1991 | Grandjean et al. | 5,226,604 A | 7/1993 | Seiffert et al. |
| 5,077,102 A | 12/1991 | Chong | 5,230,694 A | 7/1993 | Rosenblum |
| 5,077,870 A | 1/1992 | Melbye et al. | 5,233,985 A | 8/1993 | Hudrlik |
| 5,078,139 A | 1/1992 | Strand et al. | 5,235,326 A | 8/1993 | Beigel et al. |
| 5,082,006 A | 1/1992 | Jonasson et al. | 5,244,269 A | 9/1993 | Harriehausen et al. |
| 5,083,563 A | 1/1992 | Collins et al. | 5,244,461 A | 9/1993 | Derlien et al. |
| 5,084,699 A | 1/1992 | DeMichele | 5,246,008 A | 9/1993 | Mueller et al. |
| 5,085,224 A | 2/1992 | Galen et al. | 5,249,858 A | 10/1993 | Nusser |
| 5,085,258 A | 2/1992 | Fink, Jr. et al. | 5,250,020 A | 10/1993 | Bley |
| 5,089,673 A | 2/1992 | Strzodka et al. | 5,254,096 A | 10/1993 | Rondelet et al. |
| 5,089,979 A | 2/1992 | McEachern et al. | 5,256,157 A | 10/1993 | Samiotes et al. |
| 5,095,309 A | 3/1992 | Troyk et al. | 5,263,244 A | 11/1993 | Centa et al. |
| 5,096,271 A | 3/1992 | Portman | 5,263,981 A | 11/1993 | Polyak et al. |
| 5,097,831 A | 3/1992 | Lekholm | 5,267,940 A | 12/1993 | Moulder |
| 5,098,384 A | 3/1992 | Abrams | 5,267,942 A | 12/1993 | Saperston |
| 5,103,832 A | 4/1992 | Jackson | 5,269,891 A | 12/1993 | Colin et al. |
| 5,105,810 A | 4/1992 | Collins et al. | 5,271,395 A | 12/1993 | Wahlstrand et al. |
| 5,107,850 A | 4/1992 | Olive | 5,274,859 A | 1/1994 | Redman et al. |
| 5,112,344 A | 5/1992 | Petros et al. | 5,280,789 A | 1/1994 | Potts |
| 5,113,859 A | 5/1992 | Funke et al. | 5,282,839 A | 2/1994 | Roline et al. |
| 5,113,869 A | 5/1992 | Nappholz et al. | 5,282,840 A | 2/1994 | Hudrlik |
| 5,115,676 A | 5/1992 | Lee | 5,291,894 A | 3/1994 | Nagy et al. |
| 5,117,825 A | 6/1992 | Grevious | 5,292,219 A | 3/1994 | Merin et al. |
| 5,121,777 A | 6/1992 | Leininger et al. | 5,295,967 A | 3/1994 | Rondelet et al. |

| Patent No. | Date | Inventor |
|---|---|---|
| 5,298,022 A | 3/1994 | Bernardi et al. |
| 5,298,884 A | 3/1994 | Gilmore et al. |
| 5,300,093 A | 4/1994 | Koestner et al. |
| 5,300,120 A | 4/1994 | Knapp et al. |
| 5,304,112 A | 4/1994 | Mrklas et al. |
| 5,305,923 A | 4/1994 | Kirschner et al. |
| 5,312,443 A | 5/1994 | Adams et al. |
| 5,312,452 A | 5/1994 | Salo |
| 5,312,453 A | 5/1994 | Shelton et al. |
| 5,313,953 A | 5/1994 | Yomtov et al. |
| 5,314,451 A | 5/1994 | Mulier |
| 5,314,457 A | 5/1994 | Jeutter et al. |
| 5,324,315 A | 6/1994 | Grevious |
| 5,325,834 A | 7/1994 | Ballheimer et al. |
| 5,326,249 A | 7/1994 | Weissfloch et al. |
| 5,328,460 A | 7/1994 | Lord et al. |
| 5,330,511 A | 7/1994 | Boute et al. |
| 5,337,750 A | 8/1994 | Walloch |
| 5,341,430 A | 8/1994 | Aulia et al. |
| 5,342,401 A | 8/1994 | Spano et al. |
| 5,342,406 A | 8/1994 | Thompson |
| 5,344,388 A | 9/1994 | Maxwell et al. |
| 5,347,476 A | 9/1994 | McBean, Sr. |
| 5,348,210 A | 9/1994 | Linzell et al. |
| 5,348,536 A | 9/1994 | Young et al. |
| 5,350,413 A | 9/1994 | Miller et al. |
| 5,352,180 A | 10/1994 | Candelon et al. |
| 5,353,622 A | 10/1994 | Theener |
| 5,353,800 A | 10/1994 | Pohndorf et al. |
| 5,354,200 A | 10/1994 | Klein et al. |
| 5,354,316 A | 10/1994 | Keimel |
| 5,354,319 A | 10/1994 | Wyborny et al. |
| 5,360,407 A | 11/1994 | Leonard et al. |
| 5,365,462 A | 11/1994 | McBean, Sr. |
| 5,365,619 A | 11/1994 | Solomon |
| 5,365,985 A | 11/1994 | Todd et al. |
| 5,368,040 A | 11/1994 | Carney |
| 5,370,665 A | 12/1994 | Hudrlik |
| 5,373,852 A | 12/1994 | Harrison et al. |
| 5,375,073 A | 12/1994 | McBean |
| 5,377,128 A | 12/1994 | McBean |
| 5,378,231 A | 1/1995 | Johnson et al. |
| 5,382,232 A | 1/1995 | Hague et al. |
| 5,383,915 A | 1/1995 | Adams |
| 5,388,578 A | 2/1995 | Yomtov et al. |
| 5,388,586 A | 2/1995 | Lee et al. |
| 5,388,831 A | 2/1995 | Quadri et al. |
| 5,394,909 A | 3/1995 | Mitchell et al. |
| 5,402,944 A | 4/1995 | Pape et al. |
| 5,406,957 A | 4/1995 | Tansey |
| 5,409,009 A | 4/1995 | Olson |
| 5,411,031 A | 5/1995 | Yomtov |
| 5,411,551 A | 5/1995 | Winston et al. |
| 5,411,552 A | 5/1995 | Andersen et al. |
| 5,416,372 A | 5/1995 | Ljungstroem et al. |
| 5,417,226 A | 5/1995 | Juma |
| 5,417,717 A | 5/1995 | Salo et al. |
| 5,425,362 A | 6/1995 | Siker et al. |
| 5,431,171 A | 7/1995 | Harrison et al. |
| 5,431,694 A | 7/1995 | Snaper et al. |
| 5,433,694 A | 7/1995 | Lim et al. |
| 5,437,605 A | 8/1995 | Helmy et al. |
| 5,443,215 A | 8/1995 | Fackler |
| 5,447,519 A | 9/1995 | Peterson |
| 5,449,368 A | 9/1995 | Kuzmak |
| 5,456,690 A | 10/1995 | Duong-Van |
| 5,461,390 A | 10/1995 | Hoshen |
| 5,464,435 A | 11/1995 | Neumann |
| 5,467,627 A | 11/1995 | Smith et al. |
| 5,474,226 A | 12/1995 | Joseph |
| 5,479,818 A | 1/1996 | Walter et al. |
| 5,482,049 A | 1/1996 | Addiss et al. |
| 5,487,760 A | 1/1996 | Villafana |
| 5,493,738 A | 2/1996 | Sanderson et al. |
| 5,494,036 A | 2/1996 | Uber, III et al. |
| 5,494,193 A | 2/1996 | Kirschner et al. |
| 5,504,474 A | 4/1996 | Libman et al. |
| 5,505,916 A | 4/1996 | Berry, Jr. |
| 5,507,412 A | 4/1996 | Ebert et al. |
| 5,507,737 A | 4/1996 | Palmskog et al. |
| 5,507,785 A | 4/1996 | Deno |
| 5,509,888 A | 4/1996 | Miller |
| 5,509,891 A | 4/1996 | DeRidder |
| 5,513,945 A | 5/1996 | Hartmann et al. |
| 5,514,103 A | 5/1996 | Srisathapat et al. |
| 5,518,504 A | 5/1996 | Polyak |
| 5,520,606 A | 5/1996 | Schoolman et al. |
| 5,523,740 A | 6/1996 | Burgmann et al. |
| 5,534,018 A | 7/1996 | Wahlstrand et al. |
| 5,535,752 A | 7/1996 | Halperin et al. |
| 5,538,005 A | 7/1996 | Harrison et al. |
| 5,541,857 A | 7/1996 | Walter et al. |
| 5,545,140 A | 8/1996 | Conero et al. |
| 5,545,151 A | 8/1996 | O'Connor et al. |
| 5,545,186 A | 8/1996 | Olson et al. |
| 5,545,214 A | 8/1996 | Stevens |
| 5,547,470 A | 8/1996 | Johnson et al. |
| 5,551,427 A | 9/1996 | Altman |
| 5,551,439 A | 9/1996 | Hickey |
| 5,554,185 A | 9/1996 | Block et al. |
| 5,558,644 A | 9/1996 | Boyd et al. |
| 5,564,434 A | 10/1996 | Halperin et al. |
| 5,575,770 A | 11/1996 | Melsky et al. |
| 5,584,803 A | 12/1996 | Stevens et al. |
| 5,586,629 A | 12/1996 | Shoberg et al. |
| 5,593,430 A | 1/1997 | Renger |
| 5,594,665 A | 1/1997 | Walter et al. |
| 5,596,986 A | 1/1997 | Goldfarb |
| 5,597,284 A | 1/1997 | Weltlich et al. |
| 5,610,083 A | 3/1997 | Chan et al. |
| 5,611,768 A | 3/1997 | Tutrone, Jr. |
| 5,612,497 A | 3/1997 | Walter et al. |
| 5,615,671 A | 4/1997 | Schoonen et al. |
| 5,619,991 A | 4/1997 | Sloane |
| 5,625,946 A | 5/1997 | Wildeson et al. |
| 5,626,623 A | 5/1997 | Kieval et al. |
| 5,626,630 A | 5/1997 | Markowitz et al. |
| 5,630,836 A | 5/1997 | Prem et al. |
| 5,634,255 A | 6/1997 | Bishop et al. |
| 5,637,083 A | 6/1997 | Bertrand et al. |
| 5,643,207 A | 7/1997 | Rise |
| 5,645,116 A | 7/1997 | McDonald |
| 5,650,766 A | 7/1997 | Burgmann et al. |
| 5,673,585 A | 10/1997 | Bishop et al. |
| 5,676,690 A | 10/1997 | Noren et al. |
| 5,681,285 A | 10/1997 | Ford et al. |
| 5,686,831 A | 11/1997 | Vandervalk et al. |
| 5,687,734 A | 11/1997 | Dempsey et al. |
| 5,693,076 A | 12/1997 | Kaemmerer |
| 5,702,368 A | 12/1997 | Stevens et al. |
| 5,702,427 A | 12/1997 | Ecker et al. |
| 5,702,431 A | 12/1997 | Wang et al. |
| 5,704,352 A | 1/1998 | Tremblay et al. |
| 5,715,786 A | 2/1998 | Seiberth et al. |
| 5,715,837 A | 2/1998 | Chen |
| 5,718,682 A * | 2/1998 | Tucker ................ 604/288.02 |
| 5,720,436 A | 2/1998 | Buschor et al. |
| 5,730,101 A | 3/1998 | Aupperle et al. |
| 5,732,710 A | 3/1998 | Rabinovich et al. |
| 5,733,313 A | 3/1998 | Barreras, Sr. et al. |
| 5,738,652 A | 4/1998 | Boyd et al. |
| 5,742,233 A | 4/1998 | Hoffman et al. |
| 5,743,267 A | 4/1998 | Nikolic et al. |
| 5,749,369 A | 5/1998 | Rabinovich et al. |
| 5,749,909 A | 5/1998 | Schroeppel et al. |
| 5,755,687 A | 5/1998 | Donlon |
| 5,755,748 A | 5/1998 | Borza et al. |
| 5,765,568 A | 6/1998 | Sweezer, Jr. et al. |
| 5,769,812 A | 6/1998 | Stevens et al. |
| 5,771,903 A | 6/1998 | Jakobsson |
| 5,782,774 A | 7/1998 | Shmulewitz |
| 5,787,520 A | 8/1998 | Dunbar |
| 5,791,344 A | 8/1998 | Schulman et al. |
| 5,792,094 A | 8/1998 | Stevens et al. |
| 5,792,179 A | 8/1998 | Sideris |
| 5,795,325 A | 8/1998 | Valley et al. |
| 5,796,827 A | 8/1998 | Coppersmith et al. |
| 5,800,375 A | 9/1998 | Sweezer et al. |

| | | |
|---|---|---|
| 5,807,265 A | 9/1998 | Itoigawa et al. |
| 5,807,336 A | 9/1998 | Russo et al. |
| 5,810,015 A | 9/1998 | Flaherty |
| 5,810,757 A | 9/1998 | Sweezer, Jr. et al. |
| 5,814,016 A | 9/1998 | Valley et al. |
| 5,817,093 A | 10/1998 | Williamson, IV et al. |
| 5,833,603 A | 11/1998 | Kovacs et al. |
| 5,836,300 A | 11/1998 | Mault |
| 5,836,886 A | 11/1998 | Itoigawa et al. |
| 5,840,081 A | 11/1998 | Andersen et al. |
| 5,849,225 A | 12/1998 | Ebina et al. |
| 5,855,597 A | 1/1999 | Jayaraman et al. |
| 5,855,601 A | 1/1999 | Bessler et al. |
| 5,860,938 A | 1/1999 | Lafontaine et al. |
| 5,861,018 A | 1/1999 | Feierbach |
| 5,863,366 A | 1/1999 | Snow |
| 5,868,702 A | 2/1999 | Stevens et al. |
| 5,873,837 A | 2/1999 | Lieber et al. |
| 5,875,953 A | 3/1999 | Shioya et al. |
| 5,879,499 A | 3/1999 | Corvi |
| 5,881,919 A | 3/1999 | Womac et al. |
| 5,885,238 A | 3/1999 | Stevens et al. |
| 5,887,475 A | 3/1999 | Muldner |
| 5,899,927 A | 5/1999 | Ecker et al. |
| 5,916,179 A | 6/1999 | Sharrock |
| 5,916,237 A | 6/1999 | Schu |
| 5,935,078 A | 8/1999 | Feierbach |
| 5,938,669 A | 8/1999 | Klaiber et al. |
| 5,951,487 A | 9/1999 | Brehmeier-Flick et al. |
| 5,957,861 A | 9/1999 | Combs et al. |
| 5,967,986 A | 10/1999 | Cimochowski et al. |
| 5,971,934 A | 10/1999 | Scherer et al. |
| 5,974,873 A | 11/1999 | Nelson et al. |
| 5,978,985 A | 11/1999 | Thurman |
| 5,995,874 A | 11/1999 | Borza et al. |
| 6,015,386 A | 1/2000 | Kensey et al. |
| 6,015,387 A | 1/2000 | Schwartz et al. |
| 6,019,729 A | 2/2000 | Itoigawa et al. |
| 6,024,704 A | 2/2000 | Meador et al. |
| 6,030,413 A | 2/2000 | Lazarus |
| 6,035,461 A | 3/2000 | Nguyen |
| 6,053,873 A | 4/2000 | Govari et al. |
| 6,056,723 A | 5/2000 | Donlon |
| 6,058,330 A | 5/2000 | Borza et al. |
| 6,059,757 A | 5/2000 | Macoviak et al. |
| 6,067,474 A | 5/2000 | Schulman et al. |
| 6,067,991 A | 5/2000 | Forsell et al. |
| 6,076,016 A | 6/2000 | Feierbach |
| 6,083,174 A | 7/2000 | Brehmeier-Flick et al. |
| 6,090,096 A | 7/2000 | St. Goar et al. |
| 6,102,678 A | 8/2000 | Peclat et al. |
| 6,102,856 A | 8/2000 | Groff et al. |
| 6,102,922 A | 8/2000 | Jakobsson et al. |
| 6,106,477 A | 8/2000 | Miesel et al. |
| 6,106,551 A | 8/2000 | Crossett et al. |
| 6,110,145 A | 8/2000 | Macoviak |
| 6,113,553 A | 9/2000 | Chubbuck |
| 6,117,067 A * | 9/2000 | Gil-Vernet ................ 600/30 |
| 6,131,664 A | 10/2000 | Sonnier |
| 6,135,945 A | 10/2000 | Sultan |
| 6,159,156 A | 12/2000 | Van Bockel et al. |
| 6,162,180 A | 12/2000 | Miesel et al. |
| 6,162,245 A | 12/2000 | Jayaraman et al. |
| 6,168,614 B1 | 1/2001 | Andersen et al. |
| 6,190,352 B1 * | 2/2001 | Haarala et al. ............ 604/93.01 |
| 6,234,745 B1 | 5/2001 | Pugh et al. |
| 6,240,316 B1 | 5/2001 | Richmond et al. |
| 6,240,318 B1 | 5/2001 | Phillips |
| 6,245,102 B1 | 6/2001 | Jayaraman |
| 6,248,080 B1 | 6/2001 | Miesel et al. |
| 6,251,093 B1 | 6/2001 | Valley et al. |
| 6,269,819 B1 | 8/2001 | Oz et al. |
| 6,277,078 B1 | 8/2001 | Porat et al. |
| 6,292,697 B1 | 9/2001 | Roberts |
| 6,309,350 B1 | 10/2001 | VanTassel et al. |
| 6,315,769 B1 | 11/2001 | Peer et al. |
| 6,319,208 B1 | 11/2001 | Abita et al. |
| 6,328,699 B1 | 12/2001 | Eigler et al. |
| 6,338,735 B1 | 1/2002 | Stevens |
| 6,357,438 B1 | 3/2002 | Hansen |
| 6,360,122 B1 | 3/2002 | Fischell et al. |
| 6,360,822 B1 | 3/2002 | Robertson et al. |
| 6,366,817 B1 | 4/2002 | Kung |
| 6,379,308 B1 | 4/2002 | Brockway et al. |
| 6,379,380 B1 | 4/2002 | Satz |
| 6,398,752 B1 | 6/2002 | Sweezer, Jr. et al. |
| 6,409,674 B1 | 6/2002 | Brockway et al. |
| 6,423,031 B1 | 7/2002 | Donlon |
| 6,430,444 B1 | 8/2002 | Borza et al. |
| 6,431,175 B1 | 8/2002 | Penner et al. |
| 6,432,040 B1 | 8/2002 | Meah |
| 6,443,887 B1 | 9/2002 | Derus et al. |
| 6,443,893 B1 | 9/2002 | Schnakenberg et al. |
| 6,450,173 B1 | 9/2002 | Forsell et al. |
| 6,450,946 B1 | 9/2002 | Forsell et al. |
| 6,453,907 B1 | 9/2002 | Forsell et al. |
| 6,454,698 B1 | 9/2002 | Forsell et al. |
| 6,454,699 B1 | 9/2002 | Forsell et al. |
| 6,454,700 B1 | 9/2002 | Forsell et al. |
| 6,454,701 B1 | 9/2002 | Forsell et al. |
| 6,461,292 B1 | 10/2002 | Forsell et al. |
| 6,461,293 B1 | 10/2002 | Forsell et al. |
| 6,463,329 B1 | 10/2002 | Goedeke |
| 6,463,935 B1 | 10/2002 | Forsell et al. |
| 6,464,628 B1 | 10/2002 | Forsell et al. |
| 6,470,212 B1 | 10/2002 | Weijand et al. |
| 6,470,892 B1 | 10/2002 | Forsell et al. |
| 6,471,635 B1 | 10/2002 | Forsell et al. |
| 6,475,136 B1 | 11/2002 | Forsell et al. |
| 6,475,170 B1 | 11/2002 | Doron et al. |
| 6,478,783 B1 * | 11/2002 | Moorehead ............. 604/288.02 |
| 6,482,145 B1 | 11/2002 | Forsell et al. |
| 6,482,171 B1 | 11/2002 | Corvi et al. |
| 6,482,177 B1 | 11/2002 | Leinders et al. |
| 6,486,588 B2 | 11/2002 | Doron et al. |
| 6,503,189 B1 | 1/2003 | Forsell et al. |
| 6,504,286 B1 | 1/2003 | Porat et al. |
| 6,531,739 B2 | 3/2003 | Cable et al. |
| 6,533,719 B2 | 3/2003 | Kuyava et al. |
| 6,533,733 B1 | 3/2003 | Ericson et al. |
| 6,542,350 B1 | 4/2003 | Rogers |
| 6,558,321 B1 | 5/2003 | Burd et al. |
| 6,558,994 B2 | 5/2003 | Cha et al. |
| 6,573,563 B2 | 6/2003 | Lee et al. |
| 6,582,462 B1 | 6/2003 | Andersen et al. |
| 6,599,250 B2 | 7/2003 | Webb et al. |
| 6,605,112 B1 | 8/2003 | Moll et al. |
| 6,629,534 B1 | 10/2003 | St. Goar et al. |
| 6,640,137 B2 | 10/2003 | MacDonald |
| 6,641,610 B2 | 11/2003 | Wolf et al. |
| 6,645,143 B2 | 11/2003 | VanTassel et al. |
| 6,673,109 B2 | 1/2004 | Cox |
| 6,678,561 B2 | 1/2004 | Forsell et al. |
| 6,682,480 B1 | 1/2004 | Habib et al. |
| 6,682,503 B1 | 1/2004 | Fariss et al. |
| 6,682,559 B2 | 1/2004 | Myers et al. |
| 6,695,866 B1 | 2/2004 | Kuehn et al. |
| 6,709,385 B2 | 3/2004 | Forsell et al. |
| 6,718,200 B2 | 4/2004 | Marmaropoulos et al. |
| 6,719,787 B2 | 4/2004 | Cox |
| 6,719,788 B2 | 4/2004 | Cox |
| 6,719,789 B2 | 4/2004 | Cox |
| 6,731,976 B2 | 5/2004 | Penn et al. |
| 6,733,525 B2 | 5/2004 | Pease et al. |
| 6,736,846 B2 | 5/2004 | Cox |
| 6,752,813 B2 | 6/2004 | Goldfarb et al. |
| 6,796,942 B1 | 9/2004 | Kreiner et al. |
| 6,822,343 B2 | 11/2004 | Estevez |
| 6,851,628 B1 | 2/2005 | Garrison et al. |
| 6,855,115 B2 | 2/2005 | Fonseca et al. |
| 6,889,772 B2 | 5/2005 | Buytaert et al. |
| 6,890,300 B2 | 5/2005 | Lloyd et al. |
| 6,896,651 B2 | 5/2005 | Gross et al. |
| 6,896,690 B1 | 5/2005 | Lambrecht et al. |
| 6,913,600 B2 | 7/2005 | Valley et al. |
| 6,915,165 B2 | 7/2005 | Forsell et al. |
| 6,926,246 B2 | 8/2005 | Ginggen et al. |
| 6,929,653 B2 | 8/2005 | Strecter |

| | | | | | | |
|---|---|---|---|---|---|---|
| 6,932,792 B1 | 8/2005 | St. Goar et al. | | 2005/0240156 A1 | 10/2005 | Conlon |
| 6,951,229 B2 | 10/2005 | Garrison et al. | | 2005/0250979 A1 | 11/2005 | Coe |
| 6,951,571 B1 | 10/2005 | Srivastava | | 2005/0267406 A1 | 12/2005 | Hassler |
| 6,953,429 B2 | 10/2005 | Forsell et al. | | 2005/0267500 A1 | 12/2005 | Hassler et al. |
| 6,961,619 B2 | 11/2005 | Casey | | 2005/0272968 A1 | 12/2005 | Byrum et al. |
| 6,970,742 B2 | 11/2005 | Mann et al. | | 2005/0277960 A1 | 12/2005 | Hassler et al. |
| 6,979,350 B2 | 12/2005 | Moll et al. | | 2005/0277974 A1 | 12/2005 | Hassler et al. |
| 6,985,078 B2 | 1/2006 | Suzuki et al. | | 2005/0288604 A1 | 12/2005 | Eigler et al. |
| 6,989,027 B2 | 1/2006 | Allen et al. | | 2005/0288720 A1 | 12/2005 | Ross et al. |
| 7,011,095 B2 | 3/2006 | Wolf et al. | | 2005/0288721 A1 | 12/2005 | Girouard et al. |
| 7,011,624 B2 | 3/2006 | Forsell et al. | | 2005/0288739 A1 | 12/2005 | Hassler et al. |
| 7,017,583 B2 | 3/2006 | Forsell et al. | | 2005/0288740 A1 | 12/2005 | Hassler et al. |
| 7,018,406 B2 | 3/2006 | Seguin et al. | | 2005/0288741 A1 | 12/2005 | Hassler et al. |
| 7,021,402 B2 | 4/2006 | Beato et al. | | 2005/0288742 A1 | 12/2005 | Giordano et al. |
| 7,025,727 B2 | 4/2006 | Brockway et al. | | 2006/0002035 A1 | 1/2006 | Gao et al. |
| 7,044,920 B2 | 5/2006 | Letort et al. | | 2006/0010090 A1 | 1/2006 | Brockway et al. |
| 7,060,080 B2 | 6/2006 | Bachmann et al. | | 2006/0020224 A1 | 1/2006 | Geiger |
| 7,081,683 B2 | 7/2006 | Ariav et al. | | 2006/0020305 A1 | 1/2006 | Desai et al. |
| 7,108,686 B2 * | 9/2006 | Burke et al. ............... 604/891.1 | | 2006/0035446 A1 | 2/2006 | Chang et al. |
| 7,109,933 B2 | 9/2006 | Ito et al. | | 2006/0047205 A1 | 3/2006 | Ludomirsky et al. |
| 7,131,447 B2 | 11/2006 | Sterman et al. | | 2006/0049714 A1 | 3/2006 | Liu et al. |
| 7,131,945 B2 | 11/2006 | Fink et al. | | 2006/0058627 A1 | 3/2006 | Flaherty et al. |
| 7,134,580 B2 | 11/2006 | Garrison et al. | | 2006/0064134 A1 | 3/2006 | Mazar et al. |
| 7,144,400 B2 | 12/2006 | Byrum et al. | | 2006/0085051 A1 | 4/2006 | Fritsch |
| 7,147,640 B2 | 12/2006 | Huebner et al. | | 2006/0085571 A1 | 4/2006 | Gertner |
| 7,153,262 B2 | 12/2006 | Stivoric et al. | | 2006/0089619 A1 * | 4/2006 | Ginggen ............... 604/891.1 |
| 7,187,978 B2 | 3/2007 | Malek et al. | | 2006/0094966 A1 | 5/2006 | Brockway et al. |
| 7,225,032 B2 | 5/2007 | Schmeling et al. | | 2006/0100531 A1 | 5/2006 | Moser |
| 7,257,438 B2 | 8/2007 | Kinast | | 2006/0113187 A1 | 6/2006 | Deng et al. |
| 7,285,090 B2 | 10/2007 | Stivoric et al. | | 2006/0122285 A1 | 6/2006 | Fallon et al. |
| 7,608,065 B2 * | 10/2009 | Glenn ............... 604/288.02 | | 2006/0122863 A1 | 6/2006 | Gottesman et al. |
| 7,762,999 B2 * | 7/2010 | Byrum ............... 604/288.02 | | 2006/0142635 A1 | 6/2006 | Forsell |
| 2001/0011543 A1 | 8/2001 | Forsell | | 2006/0149124 A1 | 7/2006 | Forsell |
| 2001/0041823 A1 | 11/2001 | Snyder et al. | | 2006/0149324 A1 | 7/2006 | Mann et al. |
| 2002/0049394 A1 | 4/2002 | Roy et al. | | 2006/0149327 A1 | 7/2006 | Hedberg et al. |
| 2002/0120200 A1 | 8/2002 | Brockway et al. | | 2006/0157701 A1 | 7/2006 | Bauer et al. |
| 2002/0138009 A1 | 9/2002 | Brockway et al. | | 2006/0161186 A1 | 7/2006 | Hassler et al. |
| 2002/0177782 A1 | 11/2002 | Penner | | 2006/0178617 A1 | 8/2006 | Adams et al. |
| 2003/0009201 A1 | 1/2003 | Forsell | | 2006/0178695 A1 | 8/2006 | Decant et al. |
| 2003/0030893 A1 | 2/2003 | Cornelius et al. | | 2006/0183967 A1 | 8/2006 | Lechner |
| 2003/0032857 A1 | 2/2003 | Forsell | | 2006/0184206 A1 | 8/2006 | Baker et al. |
| 2003/0037591 A1 | 2/2003 | Ashton et al. | | 2006/0189887 A1 | 8/2006 | Hassler et al. |
| 2003/0045775 A1 | 3/2003 | Forsell | | 2006/0189888 A1 | 8/2006 | Hassler et al. |
| 2003/0066536 A1 | 4/2003 | Forsell | | 2006/0189889 A1 | 8/2006 | Gertner |
| 2003/0088148 A1 | 5/2003 | Forsell | | 2006/0199997 A1 | 9/2006 | Hassler et al. |
| 2003/0092962 A1 | 5/2003 | Forsell | | 2006/0211912 A1 | 9/2006 | Dlugos et al. |
| 2003/0093117 A1 | 5/2003 | Saadat | | 2006/0211913 A1 | 9/2006 | Dlugos et al. |
| 2003/0100929 A1 | 5/2003 | Forsell | | 2006/0211914 A1 | 9/2006 | Hassler et al. |
| 2003/0105385 A1 | 6/2003 | Forsell | | 2006/0217668 A1 | 9/2006 | Schulze et al. |
| 2003/0109771 A1 | 6/2003 | Forsell | | 2006/0217673 A1 | 9/2006 | Schulze et al. |
| 2003/0114729 A1 | 6/2003 | Forsell | | 2006/0235310 A1 | 10/2006 | O'Brien et al. |
| 2003/0125605 A1 | 7/2003 | Forsell | | 2006/0235439 A1 | 10/2006 | Molitor et al. |
| 2003/0125768 A1 | 7/2003 | Peter | | 2006/0235448 A1 | 10/2006 | Roslin et al. |
| 2003/0135089 A1 | 7/2003 | Forsell | | 2006/0244914 A1 | 11/2006 | Cech et al. |
| 2003/0135090 A1 | 7/2003 | Forsell | | 2006/0247682 A1 | 11/2006 | Gerber et al. |
| 2003/0136417 A1 | 7/2003 | Fonseca et al. | | 2006/0247719 A1 | 11/2006 | Maschino et al. |
| 2003/0144648 A1 | 7/2003 | Forsell | | 2006/0247721 A1 | 11/2006 | Maschino et al. |
| 2003/0163079 A1 | 8/2003 | Burnett | | 2006/0247722 A1 | 11/2006 | Maschino et al. |
| 2003/0216666 A1 | 11/2003 | Ericson et al. | | 2006/0247723 A1 | 11/2006 | Gerber et al. |
| 2004/0054352 A1 | 3/2004 | Adams et al. | | 2006/0247724 A1 | 11/2006 | Gerber et al. |
| 2004/0113790 A1 | 6/2004 | Hamel et al. | | 2006/0247725 A1 | 11/2006 | Gerber et al. |
| 2004/0133092 A1 | 7/2004 | Kain | | 2006/0252982 A1 | 11/2006 | Hassler et al. |
| 2004/0147969 A1 | 7/2004 | Mann et al. | | 2006/0293625 A1 | 12/2006 | Hunt et al. |
| 2004/0172087 A1 | 9/2004 | Forsell | | 2006/0293626 A1 | 12/2006 | Byrum et al. |
| 2004/0186396 A1 | 9/2004 | Roy et al. | | 2006/0293627 A1 | 12/2006 | Byrum et al. |
| 2004/0254537 A1 | 12/2004 | Conlon et al. | | 2007/0010790 A1 | 1/2007 | Byrum et al. |
| 2005/0015014 A1 | 1/2005 | Fonseca et al. | | 2007/0027356 A1 | 2/2007 | Ortiz |
| 2005/0025979 A1 | 2/2005 | Sandt et al. | | 2007/0027493 A1 | 2/2007 | Ben-Haim et al. |
| 2005/0027175 A1 | 2/2005 | Yang | | 2007/0067206 A1 | 3/2007 | Haggerty et al. |
| 2005/0038328 A1 | 2/2005 | Stoehrer et al. | | 2007/0070906 A1 | 3/2007 | Thakur |
| 2005/0061079 A1 | 3/2005 | Schulman | | 2007/0072452 A1 | 3/2007 | Inagaki et al. |
| 2005/0102026 A1 | 5/2005 | Turner et al. | | 2007/0081304 A1 | 4/2007 | Takeguchi |
| 2005/0159789 A1 | 7/2005 | Brockway et al. | | 2007/0156013 A1 | 7/2007 | Birk |
| 2005/0165317 A1 | 7/2005 | Turner et al. | | 2007/0161958 A1 | 7/2007 | Glenn |
| 2005/0182330 A1 | 8/2005 | Brockway et al. | | 2007/0167672 A1 | 7/2007 | Dlugos et al. |
| 2005/0187482 A1 | 8/2005 | O'Brien at al. | | 2007/0173881 A1 | 7/2007 | Birk et al. |
| 2005/0187488 A1 | 8/2005 | Wolf | | 2007/0179583 A1 | 8/2007 | Goetzinger et al. |
| 2005/0192642 A1 | 9/2005 | Forsell | | 2007/0208313 A1 | 9/2007 | Conlon et al. |
| 2005/0240155 A1 | 10/2005 | Conlon | | | | |

| | | |
|---|---|---|
| 2007/0225781 A1 | 9/2007 | Saadat et al. |
| 2008/0009680 A1 | 1/2008 | Hassler |
| 2009/0228028 A1* | 9/2009 | Coe et al. .................... 606/157 |

FOREIGN PATENT DOCUMENTS

| | | |
|---|---|---|
| CA | 1119469 | 3/1982 |
| CA | 1275135 | 10/1990 |
| CA | 1277885 | 12/1990 |
| CA | 1317482 | 5/1993 |
| CA | 2082015 | 5/1993 |
| CA | 1327191 | 2/1994 |
| CA | 2119101 | 9/1994 |
| CA | 2305998 | 4/1999 |
| CN | 1059035 | 2/1992 |
| CN | 1119469 | 3/1996 |
| CN | 1241003 | 1/2000 |
| EA | 4581 | 6/2004 |
| EP | 125387 B1 | 11/1984 |
| EP | 417171 | 3/1991 |
| EP | 508141 | 10/1992 |
| EP | 568730 | 11/1993 |
| EP | 605302 | 7/1994 |
| EP | 660482 | 6/1995 |
| EP | 714017 | 5/1996 |
| EP | 769340 | 4/1997 |
| EP | 846475 | 6/1998 |
| EP | 848780 | 6/1998 |
| EP | 876808 | 11/1998 |
| EP | 888079 | 1/1999 |
| EP | 914059 | 5/1999 |
| EP | 0941712 | 9/1999 |
| EP | 981293 | 3/2000 |
| EP | 997680 | 5/2000 |
| EP | 1003021 | 5/2000 |
| EP | 1022983 | 8/2000 |
| EP | 1050265 | 11/2000 |
| EP | 1115329 | 7/2001 |
| EP | 1119314 | 8/2001 |
| EP | 1128871 | 9/2001 |
| EP | 1202674 | 5/2002 |
| EP | 1213991 | 6/2002 |
| EP | 1253877 | 11/2002 |
| EP | 1253879 | 11/2002 |
| EP | 1253880 | 11/2002 |
| EP | 1253881 | 11/2002 |
| EP | 1253883 | 11/2002 |
| EP | 1253888 | 11/2002 |
| EP | 1255511 | 11/2002 |
| EP | 1255513 | 11/2002 |
| EP | 1255514 | 11/2002 |
| EP | 1263355 | 12/2002 |
| EP | 1263357 | 12/2002 |
| EP | 1284691 | 2/2003 |
| EP | 1374758 | 1/2004 |
| EP | 1488735 | 12/2004 |
| EP | 1500411 | 1/2005 |
| EP | 1510306 | 3/2005 |
| EP | 1518514 | 3/2005 |
| EP | 1545303 | 6/2005 |
| EP | 1547549 | 6/2005 |
| EP | 1563814 | 8/2005 |
| EP | 1568338 | 8/2005 |
| EP | 1582175 | 10/2005 |
| EP | 1582176 | 10/2005 |
| EP | 1584303 | 10/2005 |
| EP | 1586283 | 10/2005 |
| EP | 1591086 | 11/2005 |
| EP | 1593359 | 11/2005 |
| EP | 1598030 | 11/2005 |
| EP | 1609440 | 12/2005 |
| EP | 1674033 | 6/2006 |
| EP | 1736123 | 12/2006 |
| EP | 1799119 | 6/2007 |
| EP | 1815881 A1 | 8/2007 |
| EP | 1832252 A2 | 9/2007 |
| FR | 2730158 | 8/1996 |
| GB | 2355937 | 5/2001 |
| WO | WO-8911244 | 11/1989 |
| WO | WO-8911701 | 11/1989 |
| WO | WO-9004368 | 5/1990 |
| WO | WO-9511057 | 4/1995 |
| WO | WO-9715351 | 5/1997 |
| WO | WO-9733513 | 9/1997 |
| WO | WO-9833554 | 8/1998 |
| WO | WO-9835610 | 8/1998 |
| WO | WO-9901063 | 1/1999 |
| WO | WO-9918850 | 4/1999 |
| WO | WO-0004945 | 2/2000 |
| WO | WO-0009047 A1 | 2/2000 |
| WO | WO-0033738 | 6/2000 |
| WO | WO-0072899 | 12/2000 |
| WO | WO-0104487 | 1/2001 |
| WO | WO-0108597 | 2/2001 |
| WO | WO-0112075 | 2/2001 |
| WO | WO-0112076 | 2/2001 |
| WO | WO-0112077 | 2/2001 |
| WO | WO-0112078 | 2/2001 |
| WO | WO-0121066 | 3/2001 |
| WO | WO-0136014 | 5/2001 |
| WO | WO-0145485 | 6/2001 |
| WO | WO-0145486 | 6/2001 |
| WO | WO-0147431 | 7/2001 |
| WO | WO-0147432 | 7/2001 |
| WO | WO-0147433 | 7/2001 |
| WO | WO-0147434 | 7/2001 |
| WO | WO-0147435 | 7/2001 |
| WO | WO-0147440 | 7/2001 |
| WO | WO-0147575 | 7/2001 |
| WO | WO-0148451 | 7/2001 |
| WO | WO-0149245 | 7/2001 |
| WO | WO-0150832 | 7/2001 |
| WO | WO-0150833 | 7/2001 |
| WO | WO-0154626 | 8/2001 |
| WO | WO-0158388 | 8/2001 |
| WO | WO-0158390 | 8/2001 |
| WO | WO-0158391 | 8/2001 |
| WO | WO-0158393 | 8/2001 |
| WO | WO-0160453 | 8/2001 |
| WO | WO-0181890 | 11/2001 |
| WO | WO-0200118 | 1/2002 |
| WO | WO-0215769 | 2/2002 |
| WO | WO-0226161 | 4/2002 |
| WO | WO-02053228 | 7/2002 |
| WO | WO-02055126 | 7/2002 |
| WO | WO-02058551 | 8/2002 |
| WO | WO-02065894 | 8/2002 |
| WO | WO-02076289 | 10/2002 |
| WO | WO-02082984 | 10/2002 |
| WO | WO-02089655 | 11/2002 |
| WO | WO-02090894 | 11/2002 |
| WO | WO-02100481 | 12/2002 |
| WO | WO-03002192 | 1/2003 |
| WO | WO-03002193 | 1/2003 |
| WO | WO-03020182 | 3/2003 |
| WO | WO-03061467 | 7/2003 |
| WO | WO-03061504 | 7/2003 |
| WO | WO-03096889 | 11/2003 |
| WO | WO-2004014245 A1 | 2/2004 |
| WO | WO-2004014456 | 2/2004 |
| WO | WO-2004019773 | 3/2004 |
| WO | WO-2004058101 | 7/2004 |
| WO | WO-2004066879 | 8/2004 |
| WO | WO-2004110263 | 12/2004 |
| WO | WO-2005000206 | 1/2005 |
| WO | WO-2005007075 | 1/2005 |
| WO | WO-2005107583 | 11/2005 |
| WO | WO-2006001851 | 1/2006 |
| WO | WO-2006035446 | 4/2006 |
| WO | WO-2006108203 A2 | 10/2006 |
| WO | WO-2006113187 | 10/2006 |
| WO | WO-2006118790 A2 | 11/2006 |
| WO | WO-2006122285 | 11/2006 |
| WO | WO-2007067206 | 6/2007 |
| WO | WO-2007070906 | 6/2007 |
| WO | WO-2007072452 | 6/2007 |
| WO | WO-2007081304 | 7/2007 |
| WO | WO-2007104356 | 9/2007 |

OTHER PUBLICATIONS

"Application Specific Integrated Circuits (ASICs)", Honeywell product information from website http://www.honeywell.com/sites/portal?smap=aerospace&page=Radiation-Hardened-Electronics3&theme=T18&catID=CE06BEF88-65F8-6A1E-4ED1-6A1EC1B7AE7A&id=HA0E380D3-C27B-9EBF-AAC8-9FAF8851256D&sel=1&sel4=1; 1 page.

"Rad Hard Aerospace Components Products", Honeywell product and service information from website http://www.honeywell.com/sites/portal?smap=aerospace&page=Radiation-Hardened-Electronics3&theme=T6&catID=C815147E4-8786-29FE-49EB-C21C8790AA99&id=H0166BA51-5344-E57E-5C37-C6333EA43F61&sel=1; 1 page.

"Radiation Hardened Electronics and Radiation Technology", Honeywell product and service information from website http://www.honeywell.com/sites/portal?smap=aerospace&page=Radiation-Hardened-Electronics&theme=T4; 2 pages.

Kirchner, G., "Honeywell and Synopsys: Concept-to-Parts Solutions for Next Generation Rad-Hard ASICs", in online magazine Compiler, http://www.synopsys.com/news/pubs/compiler/artlead_redasic-apr05.html, Apr. 2005, 5 pages.

P.A. Neukomm and H. Kundig, "Passive Wireless Actuator Control and Sensor Signal Transmission," Sensors and Actuators, A21-A23 (1990) 258-262.

European Search Report, Application No. 08253986.7, Issued Mar. 30, 2009, 5 pages.

Keidar et al., "Port Complications following Laparoscopic Adjustable Gastric Banding for Morbid Obesity," Obesity Surgery, vol. 15, 2006.

Sussmallian et al., "Access-Port Complications after Laparoscopic Gastric Banding," Obesity Surgery, vol. 13, 2003.

* cited by examiner

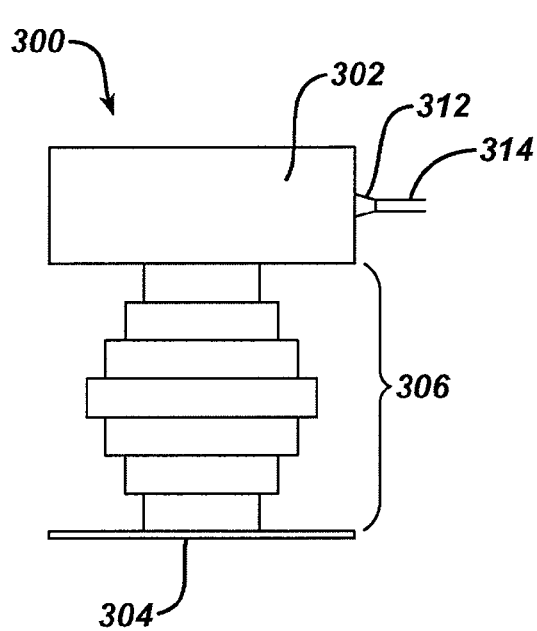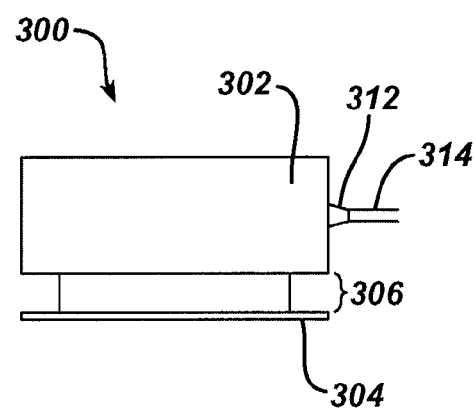
FIG. 13  FIG. 14

ADJUSTABLE HEIGHT GASTRIC RESTRICTION DEVICES AND METHODS

FIELD OF THE INVENTION

The present invention relates to devices and methods for adjusting the height of devices in a gastric restriction system.

BACKGROUND OF THE INVENTION

Obesity is becoming a growing concern, particularly in the United States, as the number of obese people continues to increase and more is learned about the negative health effects of obesity. Morbid obesity, in which a person is 100 pounds or more over ideal body weight, in particular poses significant risks for severe health problems. Accordingly, a great deal of attention is being focused on treating obese patients. One method of treating morbid obesity has been to place a restriction device, such as an elongated band, about the upper portion of the stomach. Gastric bands have typically comprised a fluid-filled elastomeric balloon with fixed endpoints that encircles the stomach just inferior to the esophageal-gastric junction to form a small gastric pouch above the band and a reduced stoma opening in the stomach. When fluid is infused into the balloon, the band expands against the stomach creating a food intake restriction or stoma in the stomach. To decrease this restriction, fluid is removed from the band. The effect of the band is to reduce the available stomach volume and thus the amount of food that can be consumed before becoming "full."

Food restriction devices have also comprised mechanically adjusted bands that similarly encircle the upper portion of the stomach. These bands include any number of resilient materials or gearing devices, as well as drive members, for adjusting the bands. Additionally, gastric bands have been developed that include both hydraulic and mechanical drive elements. An example of such an adjustable gastric band is disclosed in U.S. Pat. No. 6,067,991, entitled "Mechanical Food Intake Restriction Device" which issued on May 30, 2000, and is incorporated herein by reference. It is also known to restrict the available food volume in the stomach cavity by implanting an inflatable elastomeric balloon within the stomach cavity itself. The balloon is filled with a fluid to expand against the stomach walls and, thereby, decrease the available food volume within the stomach.

With each of the above-described food restriction devices, safe, effective treatment requires that the device be regularly monitored and adjusted to vary the degree of restriction applied to the stomach. With banding devices, the gastric pouch above the band will substantially increase in size following the initial implantation. Accordingly, the stoma opening in the stomach must initially be made large enough to enable the patient to receive adequate nutrition while the stomach adapts to the banding device. As the gastric pouch increases in size, the band may be adjusted to vary the stoma size. In addition, it is desirable to vary the stoma size in order to accommodate changes in the patient's body or treatment regime, or in a more urgent case, to relieve an obstruction or severe esophageal dilatation. Traditionally, adjusting a hydraulic gastric band required a scheduled clinician visit during which a hypodermic needle and syringe were used to permeate the patient's skin and add or remove fluid from the balloon. More recently, implantable pumps have been developed which enable non-invasive adjustments of the band. An external programmer communicates with the implanted pump using telemetry to control the pump. During a scheduled visit, a physician places a hand-held portion of the programmer near the gastric implant and transmits power and command signals to the implant. The implant in turn adjusts the fluid levels in the band and transmits a response command to the programmer.

During these gastric band adjustments, it has been difficult to determine how the adjustment is proceeding, and whether the adjustment will have the intended effect. In an attempt to determine the efficacy of an adjustment, some physicians have utilized fluoroscopy with a Barium swallow as the adjustment is being performed. However, fluoroscopy is both expensive and undesirable due to the radiation doses incurred by both the physician and patient. Other physicians have instructed the patient to drink a glass of water during or after the adjustment to determine whether the water can pass through the adjusted stoma. This method, however, only assures that the patient is not obstructing, and does not provide any information about the efficacy of the adjustment. Oftentimes, a physician may simply adopt a "try as you go" method based upon their prior experience, and the results of an adjustment may not be discovered until hours or days later, when the patient experiences a complete obstruction of the stomach cavity, or the band induces erosion of the stomach tissue.

Additionally, a gastric band adjustment can be complicated by difficult accessibility of implanted gastric band elements. Gastric band elements are typically initially secured beneath layers of fat tissue that can make the elements difficult to locate. As the patient loses weight, the elements can shift within the body, causing patient discomfort and/or making the elements harder for a physician to locate and access.

Accordingly, methods and devices are provided for use with a gastric restriction device, and in particular for accessing gastric restriction elements.

SUMMARY OF THE INVENTION

The present invention generally provides methods and devices for adjusting the height of devices in a gastric restriction system. In one embodiment, a restriction system for forming a restriction in a patient is provided that includes an implantable restriction device that can form a restriction in a patient. The system also includes an implantable housing coupled to the implantable restriction device and having an adjustable height. The housing can be in fluid communication with the implantable restriction device and include, for example, a fill port that can receive fluid from a fluid source external to the patient for delivering fluid to the implantable restriction device. In other embodiments, the housing can include a pressure sensor that can sense a pressure of fluid within the implantable restriction device and communicate pressure data to an external monitor. The housing can be at least partially formed from a bioabsorbable material (e.g., polylactide, polyglycolide, poly(lactide-co-glycolide), polyanhydride, and polyorthoester) operable to adjust the height of the housing over time.

The system can also include a coupling element extending between a base of the housing and a body of the housing. The coupling element can alter a distance between the base and the body to thereby adjust the height of the housing. The coupling element can be movable between at least two successive positions in which the housing has a height that lowers with each successive position of the coupling element.

The coupling element can have a variety of configurations, such as a collapsible structure, a retractable cord, and a fluid-filled chamber in which a change of fluid volume within the chamber can alter the distance between the base and the body. Another coupling element configuration includes a depressible element, e.g., a button formed on one of the housing's body and base, that can be depressed to move the coupling element between at least two successive positions. In other embodiments, the coupling element includes at least one flexible tab extending between the base and the body that can maintain the housing in one or more successive positions. In some embodiments, the coupling element includes a compliant mechanism (e.g., a spring) compressible to decrease the distance between the base and the body. The coupling element can further include a rack that is coupled to the compliant mechanism and that includes a plurality of teeth. A pawl can engage the rack for maintaining the housing at a selected height.

In another embodiment, a restriction system for forming a restriction in a patient includes an implantable restriction device that can form a restriction in a patient and an implantable housing coupled to the implantable restriction device. The housing has a body and a base that are movably coupled to one another to allow a height of the housing to be adjusted. The base can be formed from a bioabsorbable material that can adjust the height of the housing over time. In some embodiments, the system also includes a coupling element extending between the base and the body that can alter a distance between the base and the body to thereby adjust the height of the housing. The coupling element can be movable between at least two successive positions in which the housing has a height that lowers with each successive position of the coupling element.

In other aspects, a method of forming a restriction in a patient is provided. The method includes implanting a restriction device in a patient to form a restriction and adjusting a height of a housing coupled to the restriction device and implanted within tissue to lower a profile of the housing. Adjusting a height of the housing can include adjusting a coupling element extending between a base of the housing and a body of the housing. In other embodiments, adjusting a height of the housing includes allowing the housing to biomedically degrade within the patient.

BRIEF DESCRIPTION OF THE DRAWINGS

The invention will be more fully understood from the following detailed description taken in conjunction with the accompanying drawings, in which:

FIG. 13 is a schematic view of another embodiment of an implantable housing having a collapsible structure, shown in an expanded position;

FIG. 14 is a schematic view of the implantable housing of FIG. 13 showing the collapsible structure in a collapsed position;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods for adjusting the height of devices in a gastric restriction system. In general, the devices and methods allow one or more implantable housings coupled to an implantable restriction device to have an adjustable height. The housing can include, for example, a fill port housing, a sensor housing, and any other type of housing that can be used in an implantable restriction system and desired to have an adjustable height. The housing can lower in profile over time, e.g., as the patient loses weight, thereby maintaining the housing in a generally predictable location where it can be found and accessed. The profile can automatically adjust internal to the patient, thereby reducing or eliminating the need for invasive, expensive, time-consuming, or risky procedures involving adjustment of the gastric restriction system. The housing can instead or in addition be manually adjusted in height from outside the patient to, for example, relieve patient discomfort. Furthermore, the housing can include a base that secures the housing to the patient's fascia and a body that includes the functionality of the housing near the patient's skin surface. The housing's base and body can be separated by a distance and connected by a coupling element that can operate to alter the distance between the body and the base. In this way, the housing body can maintain its generally predictable location while the housing lowers in profile over time.

Figure 1A:
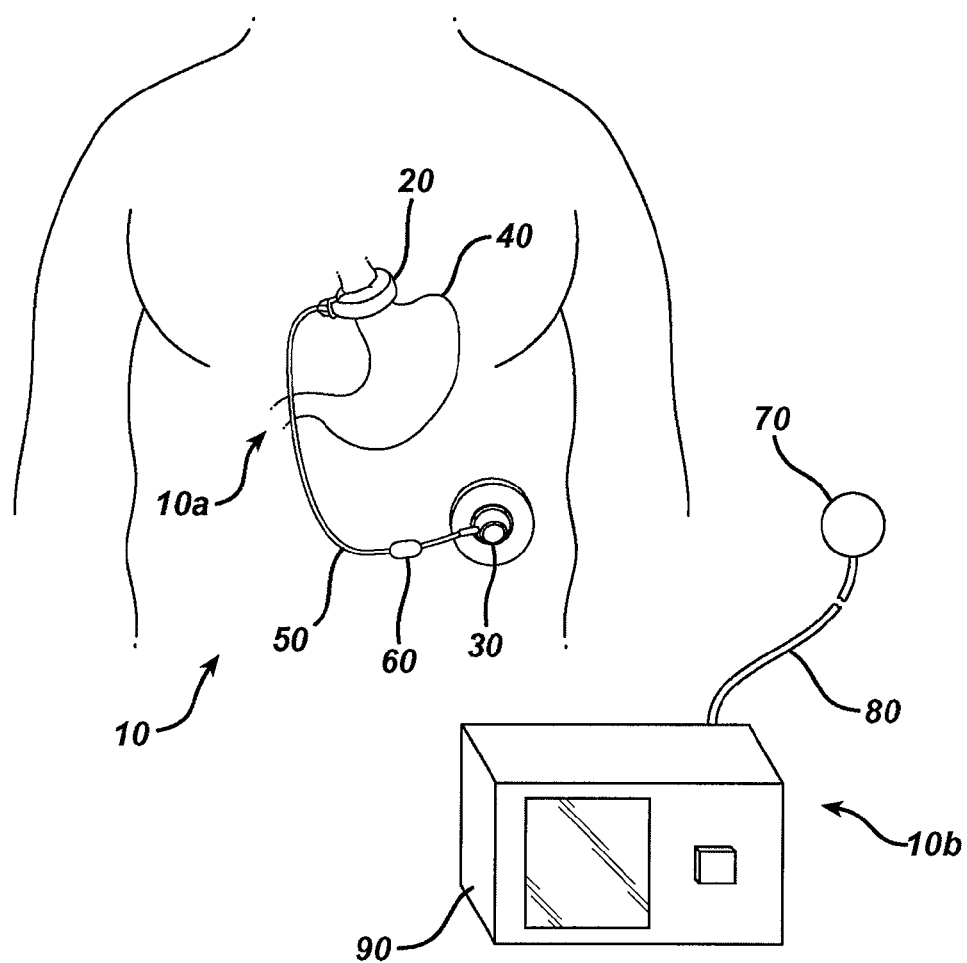
FIG. 1A is a schematic diagram of an embodiment of a food intake restriction system.
Figure 1B:
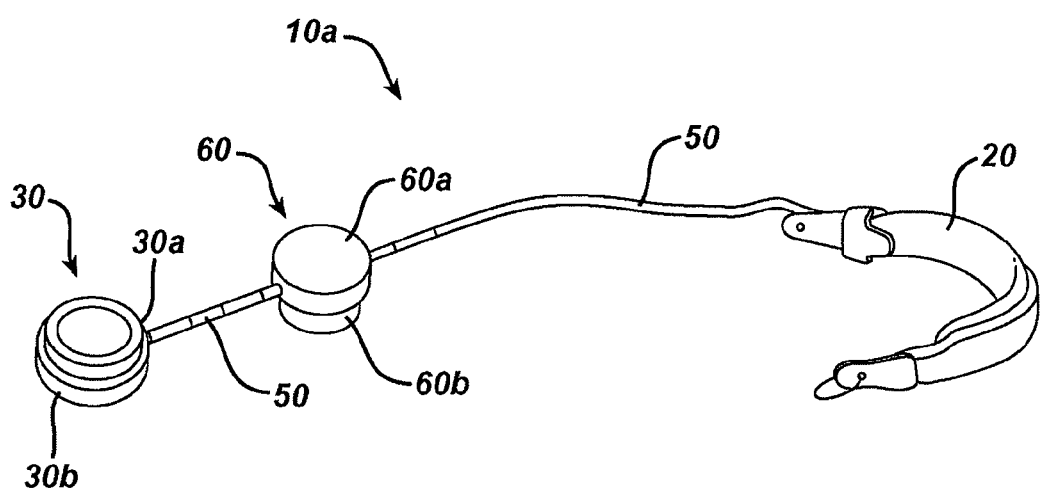
FIG. 1B is a perspective view of an embodiment of an implantable portion of the food intake restriction system of FIG. 1.

While the present invention can be used with a variety of restriction systems known in the art, FIG. 1A illustrates one exemplary embodiment of a food intake restriction system 10 in use in a patient. As shown, the system 10 generally includes an implantable portion 10a and an external portion 10b. FIG. 1B illustrates the implantable portion 10a outside of a patient. The implantable portion 10a includes an adjustable gastric band 20 that is configured to be positioned around the upper portion of a patient's stomach 40, and an injection port housing 30 that is fluidly coupled to the adjustable gastric band 20, e.g., via a catheter 50.

The injection port housing 30 can include a port body 30a and a port base 30b that are coupled together, although the port body 30a and the port base 30b can be separated by a distance. The injection port housing 30, through the port body 30a, is adapted to allow fluid to be introduced into and removed from the gastric band 20 to thereby adjust the size of the band and thus the pressure applied to the stomach. The injection port housing 30 is adapted to be fixed to the patient at the port base 30b, which can be implanted at a location within the body that allows the port body 30a to be accessible through the tissue. Typically, injection port housings are fixated to the patient in the lateral subcostal region of the patient's abdomen under the skin and layers of fatty tissue. Surgeons also typically fix injection port housings on the sternum of the patient. Wherever implanted, the injection port housing 30 can be adjusted in height as described further below.

The internal portion 10a can also include a pressure sensing or measuring device in fluid communication with the closed fluid circuit in the implantable portion 10a such that the pressure measuring device can measure the fluid pressure of the closed fluid circuit. While the pressure measuring device can have various configurations and it can be positioned anywhere along the internal portion 10a, including within the injection port housing 30, in the illustrated embodiment the pressure measuring device is in the form of a pressure sensor that is disposed within a sensor housing 60 positioned adjacent to the injection port housing 30. More specifically, the pressure sensor in this embodiment can be disposed in a sensor body 60a of the sensor housing 60, which also includes a sensor base 60b that can be fixed to the patient and be coupled to the sensor body 60a. The catheter 50 can include a first portion that is coupled between the gastric band 20 and the pressure sensor housing 60, and a second portion that is coupled between the pressure sensor housing 60 and the injection port housing 30. Although in this embodiment both the port housing 30 and the sensor housing 60 are shown having body and base portions, in some embodiments, only one of the housings in the implantable portion 10a (the port housing 30, the sensor housing 60, or another housing) may have such a base and body to adjust the housing's height.

As further shown in FIG. 1A, the external portion 10b generally includes a pressure reading device 70 that is configured to be positioned on the skin surface above the pressure sensor housing 60 (which can be fixed to the patient beneath thick tissue, e.g., over 10 cm thick) to non-invasively communicate with the pressure measuring device and thereby obtain pressure measurements. The pressure reading device 70 can optionally be electrically coupled (in this embodiment via an electrical cable assembly 80) to a control box 90 that can display the pressure measurements, or other data obtained from the pressure reading device 70.

Figure 2A:
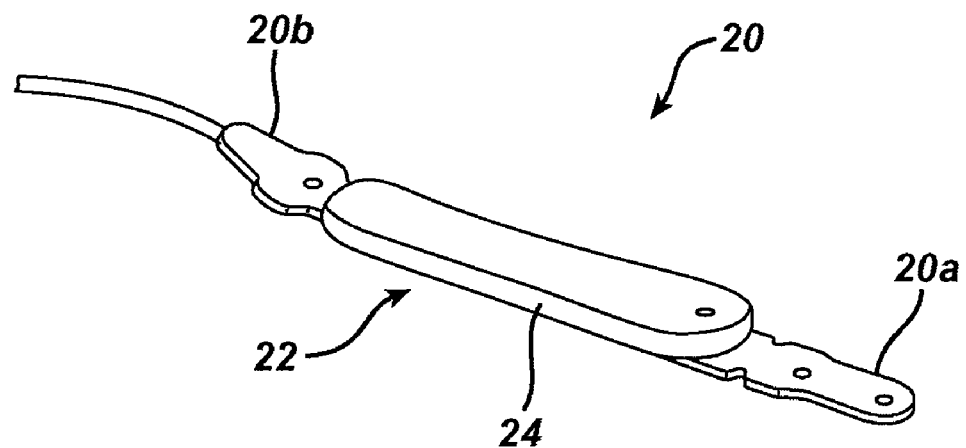
FIG. 2A is a perspective view of the food intake restriction device of FIG. 1.

FIG. 2A shows the gastric band 20 in more detail. While the gastric band 20 can have a variety of configurations, and various gastric bands currently known in the art can be used with the present invention, in the illustrated embodiment the gastric band 20 has a generally elongate shape with a support structure 22 having first and second opposite ends 20a, 20b that can be secured to each other. Various mating techniques can be used to secure the ends 20a, 20b to one another. In the illustrated embodiment, the ends 20a, 20b are in the form of straps that mate together, with one laying on top of the other. In another embodiment, illustrated in FIG. 1B, a support structure at one end of the gastric band 20 can include an opening through which the other end of the gastric band 20 can feed through to secure the ends to one another. The gastric band 20 can also includes a variable volume member, such as an inflatable balloon 24, that is disposed or formed on one side of the support structure 22 and that is configured to be positioned adjacent to tissue. The balloon 24 can expand or contract against the outer wall of the stomach to form an adjustable stoma for controllably restricting food intake into the stomach.

A person skilled in the art will appreciate that the gastric band can have a variety of other configurations. Moreover, the various methods and devices disclosed herein have equal applicability to other types of implantable bands. For example, bands are used for the treatment of fecal incontinence, as described in U.S. Pat. No. 6,461,292 which is hereby incorporated herein by reference. Bands can also be used to treat urinary incontinence, as described in U.S. Patent Application 2003/0105385 which is hereby incorporated herein by reference. Bands can also be used to treat heartburn and/or acid reflux, as disclosed in U.S. Pat. No. 6,470,892 which is hereby incorporated herein by reference. Bands can also be used to treat impotence, as described in U.S. Patent Application 2003/0114729 which is hereby incorporated herein by reference.

Figure 2B:
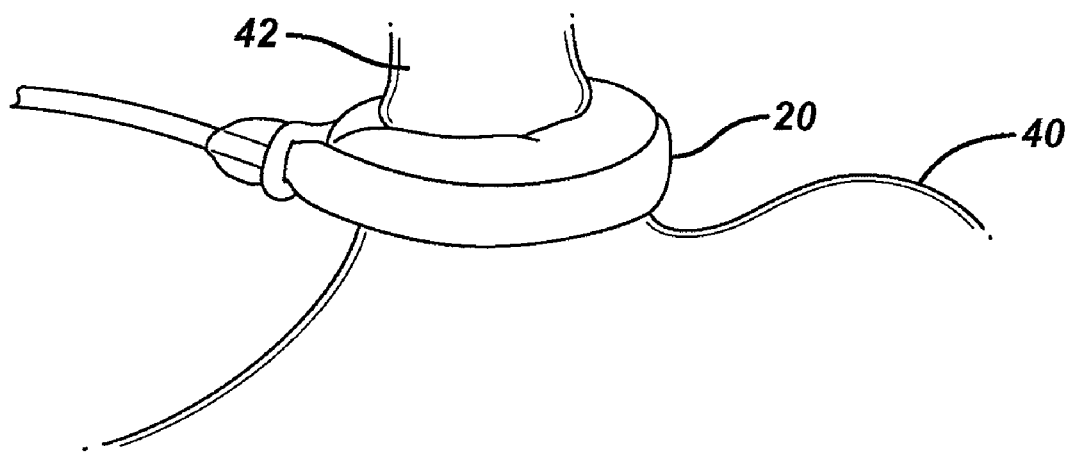
FIG. 2B is a schematic diagram of the food intake restriction device of FIG. 2A applied about the gastro-esophageal junction of a patient.

FIG. 2B shows the adjustable gastric band 20 applied about the gastro-esophageal junction of a patient. As shown, the band 20 at least substantially encloses the upper portion of the stomach 40 near the junction with the esophagus 42. After the band 20 is implanted, preferably in the deflated configuration wherein the band 20 contains little or no fluid, the band 20 can be inflated, e.g., using saline, to decrease the size of the stoma opening. A person skilled in the art will appreciate that various techniques, including mechanical and electrical techniques, can be used to adjust the band.

The fluid injection port housing 30 can also have a variety of configurations. In the embodiment shown in FIG. 3, the port body 30a and the port base 30b of the injection port housing 30 each have a generally cylindrical shape. The port body 30a can at least partially surround the port base 30b, as shown. Additionally, the port body 30a and the port base 30b are shown compressed together in FIG. 3, but the port body 30a and the port base 30b can be separated by a distance. The port body 30a can couple with the port base 30b in a variety of ways, described further below, that generally allow the housing 30 to have an adjustable height such that the port body 30a can maintain proximity to a surface of the patient's skin while the port base 30b fixes the port housing 30 to the patient at a location that can be, and typically is initially following implantation of the housing 30, remote from the port body 30a.

The port body 30a has a distal or bottom surface and a perimeter wall extending proximally from the bottom surface and defining a proximal opening 32. The proximal opening 32 can include a needle-penetrable septum 34 extending there across and providing access to a fluid reservoir (not visible in FIG. 3) formed within the port body 30a. The septum 34 is preferably placed in a proximal enough position such that the depth of the reservoir is sufficient enough to expose the open tip of a needle, such as a Huber needle, so that fluid transfer can take place. The septum 34 is preferably arranged so that it will self seal after being punctured by a needle and the needle is withdrawn.

Figure 3:
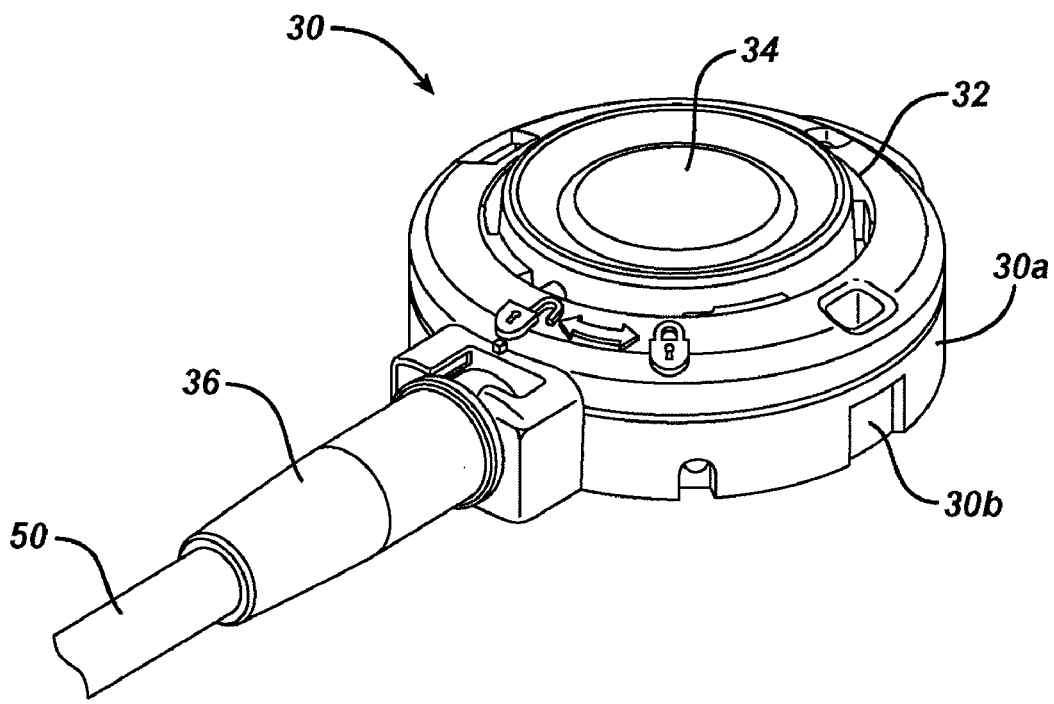
FIG. 3 is a perspective view of an embodiment of the injection port housing of FIG. 1.

As further shown in FIG. 3, the port housing 30 can further include a catheter tube connection member 36 that is in fluid communication with the reservoir and that is configured to couple to the catheter 50. A person skilled in the art will appreciate that the housing 30 can be made from any number of materials, including stainless steel, titanium, or polymeric materials, and the septum 34 can likewise be made from any number of materials, including silicone.

Figure 4:
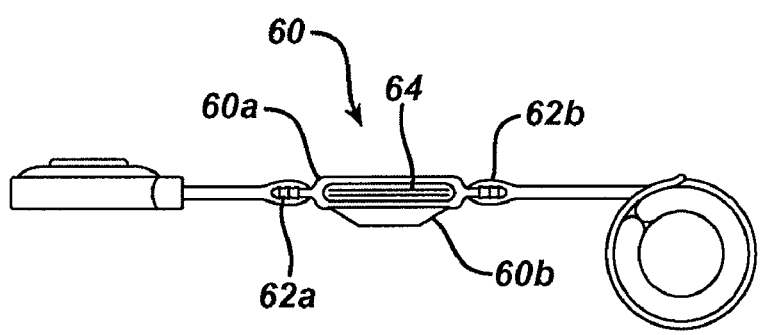
FIG. 4 is a perspective view of an embodiment of the sensor housing of FIG. 1.

As indicated above, the system 10 can also include a pressure measuring device 64, as shown in FIG. 4, that is in communication with the closed fluid circuit and that is configured to measure the fluid pressure, which corresponds to the amount of restriction applied by the adjustable gastric band 10 to the patient's stomach 40. Measuring the fluid pressure enables a physician to evaluate the restriction created by a band adjustment. In the illustrated embodiment, the pressure measuring device 64 is in the form of a pressure sensor that is disposed within the sensor body 60a of the sensor housing 60. The pressure measuring device 64 can, however, be disposed anywhere within the closed hydraulic circuit of the implantable portion 10a, and various exemplary locations and configurations are disclosed in more detail in commonly-owned U.S. Publication No. 2006/0211913 entitled "Non-Invasive Pressure Measurement In a Fluid Adjustable Restrictive Device," filed on Mar. 7, 2006, and hereby incorporated by reference in its entirety.

In general, the illustrated sensor housing 60 includes an inlet 62a and an outlet 62b, both typically part of the sensor body 60a, that are in fluid communication with the fluid in the system 10. A sensor 64 is disposed within the sensor housing 60 and is configured to respond to fluid pressure changes within the hydraulic circuit and convert the pressure changes into a usable form of data. While not shown, the pressure sensing system can also include a microcontroller, a TET/telemetry coil, and a capacitor. Optionally, the pressure sensing system can further comprise a temperature sensor (not shown). The microcontroller, the TET/telemetry coil, and the capacitor can be in communication via a circuit board (not shown) or any via any other suitable component(s). It will also be appreciated that the TET/telemetry coil and the capacitor may collectively form a tuned tank circuit for receiving power from external portion, and transmitting the pressure measurement to the pressure reading device 70.

Various pressure sensors known in the art can be used, such as a wireless pressure sensor provided by CardioMEMS, Inc. of Atlanta, Ga., though a suitable MEMS pressure sensor may be obtained from any other source, including but not limited to Integrated Sensing Systems, Inc. (ISSYS) of Ypsilanti, Mich., and Remon Medical Technologies, Inc. of Waltham, Mass. One exemplary MEMS pressure sensor is described in U.S. Pat. No. 6,855,115, the disclosure of which is incorporated by reference herein for illustrative purposes only. It will also be appreciated that suitable pressure sensors may include, but are not limited to, capacitive, piezoresistive, silicon strain gauge, or ultrasonic (acoustic) pressure sensors, as well as various other devices capable of measuring pressure.

The pressure reading device 70 can also have a variety of configurations, and one exemplary pressure reading device is disclosed in more detail in commonly-owned U.S. Publication No. 2006/0189888 and U.S. Publication No. 2006/0199997, which are hereby incorporated by reference in its entirety. In general, the pressure reading device 70 can non-invasively measure the pressure of the fluid within implanted portion even when the injection port housing 30 or the pressure measuring device 64 is implanted beneath thick (at least over 10 cm) subcutaneous fat tissue. The physician may hold pressure-reading device 70 against the patient's skin near the location of the pressure measuring device 64 and observe the pressure reading on a display on the control box 90. The housing including the pressure measuring device 64 can be palpably located near a surface of the patient's skin, typically at or near an expected location of the housing's body which can substantially maintain its location if and/or when the profile of the housing lowers. The pressure reading device 70 can also be removably attached to the patient, such as during a prolonged examination, using straps, adhesives, and other well-known methods. The pressure reading device 70 can operate through conventional cloth or paper surgical drapes, and can also include a disposal cover (not shown) that may be replaced for each patient.

FIGS. 5-16 illustrate embodiments of housings that each include a body and a base. Some embodiments also include at least one coupling element extending between the body and the base. The housing, the base, and the body are similar to those described with reference to similarly named elements of FIGS. 1A-4. Furthermore, the embodiments in FIGS. 5-16 can include variations as described herein. Generally, the housing body seats an implantable restriction system element, e.g., a fill port or a sensor, that can be in fluid communication with one or more other elements included in the implantable restriction system. The housing base couples the housing to the patient using any fixation technique, e.g., sutures. The housing's body and base are movably coupled to one another to allow adjustment of the housing's height up and/or down from a first height to a second height that can be less than or greater than the first height depending on whether the housing's height is being, respectively, decreased or increased. The housing can have any number of additional heights between the first and second heights, with a height being less than the preceding height(s) if the housing's height is being decreased or more than the preceding height(s) if the housing's height is being increased. A housing height can be more than one or more preceding heights if the housing profile is being increased to, for example, adjust a patient's treatment regime. Maximum and minimum heights of the housing can vary, but in some embodiments, the housing's height ranges from about 1 cm to 3 cm.

Referring first to FIGS. 5-9, embodiments of a housing 100 each include a housing body 102, a housing base 104, and at least one coupling element extending between the body 102 and the base 104 that can be operable to alter a distance between the body 102 and the base 104 to thereby adjust the height of the housing 100. The coupling element is substantially disposed in the housing 100, e.g., in an internal cavity 106 defined by an interior surface 108 of the body 102 and an interior surface 110 of the base 104. The surfaces 108, 110 can define the internal cavity 106 to have a fluid-tight seal. The body's interior surface 108 and the base's interior surface 110 are shaped to slidably couple the body 102 and the base 104 together. The internal cavity 106 extends around a perimeter the housing 100, which in these embodiments is a circular circumference around the substantially cylindrical housing 100. The internal cavity 106 can, in other embodiments, extend around only a portion of the housing's perimeter and/or be divided into two or more individual internal cavities. The body's interior surface 108 and the base's posterior surface 110 also define a second internal cavity 112, in a central region of the housing 100. The internal cavities 106, 112 can be in fluid communication in some embodiments. Additionally, the internal cavities 106, 112 can each have any shape and size. The height of the housing 100 can be adjusted through manipulation of the coupling element in the internal cavity 106 from outside the patient, e.g., as controlled by a physician. The housing 100 can couple to a patient at one or more locations on an outer surface 136 in a proximal portion 138 of the housing base 104.

Figure 5:
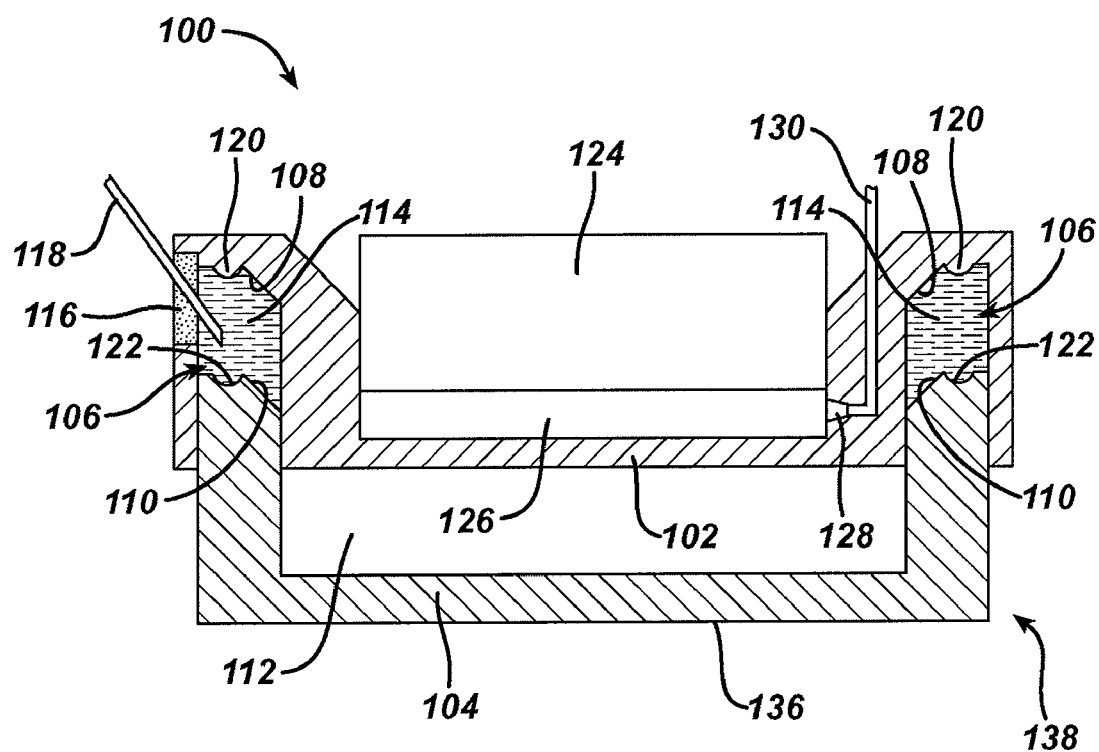
FIG. 5 is a cross-sectional schematic view of an embodiment of an implantable port housing having fluid disposed in an internal cavity of the housing.

As illustrated in FIG. 5, one example of a coupling element includes a fluid 114 (e.g., a liquid such as saline or a gas such as carbon dioxide) disposed in the internal cavity 106 between the body 102 and the base 104. The fluid 114 typically includes any type of biocompatible material appropriate for use in a body to minimize patient harm in the uncommon occurrence of housing rupture or other unintended fluid leakage. The internal cavity 106, and hence any fluid it contains, can be accessed through a housing membrane 116 on the housing body 102. The housing membrane 116 can be fluid-sealed using a bellows. The fluid 114 is typically initially introduced to the internal cavity 106 through the housing membrane 116 after the housing 100 has been implanted, although the internal cavity 106 can contain the fluid 114 before the housing's implantation. The housing base 104 can also have a housing membrane providing access to the internal cavity 106 in addition to or instead of the housing membrane 116 on the housing body 102. The housing membrane 116 is similar to the port's needle-penetrable septum 34 of FIG. 3, allowing a needle 118, such as Huber needle, to puncture the housing membrane 116 and self seal when the needle 118 is withdrawn. When a fluid volume changes in the internal cavity 106, such as by drawing fluid through the needle 118, a height between the housing body 102 and the housing base 104 can decrease. In other words, when at least a portion of the fluid 114 is evacuated from the internal cavity 106, the housing's profile can lower as the base's interior surface 110 moves closer to the body's interior surface 108 and occupies some of the internal cavity 106 space previously occupied by the fluid 114.

Enough of the fluid 114 can be removed from the internal cavity 106 such that the body 102 and the base 104 can lock together via a locking mechanism when the base 102 and the body 104 are in sufficient proximity of each other, e.g., when the coupling element draws the base 102 and the body 104 together and/or the body 102 and the base 104 are physically compressed together. Examples of locking mechanisms include a snap locking mechanism (as shown in FIG. 5) and a compression press fit. The body's interior surface 108 in this embodiment includes at least one protrusion 120 that can lock in at least one corresponding depression 122 in the base's inferior surface 110. In this embodiment, the protrusion 120 and the depression 122 extend around the housing's perimeter, although the housing 100 can include any number of corresponding protrusions and depressions anywhere in the interior surfaces 108, 110, including in the second internal cavity 112.

The embodiment of the housing 100 shown in FIG. 5 is a port housing (e.g., the port housing 30) having a septum 124 and a reservoir 126 seated in the housing body 102 (e.g., in a proximal opening of the housing 100). The housing body 102 also includes a barb-fitted connection member 128 (e.g., the catheter tube connection member 36) that is in fluid communication with the reservoir 126 and that is configured to couple to a catheter 130 (e.g., the catheter 50). The connection member 128 can be coupled to the housing body 102 at any location. Moreover, in some embodiments discussed further below, the housing base 104 can have a slotted or otherwise cut-out area in its perimeter (in which case the housing base 104 may not be completely circumferential) to allow the connection member 128 and/or the catheter 130 to extend from the housing body 102.

Figure 6:
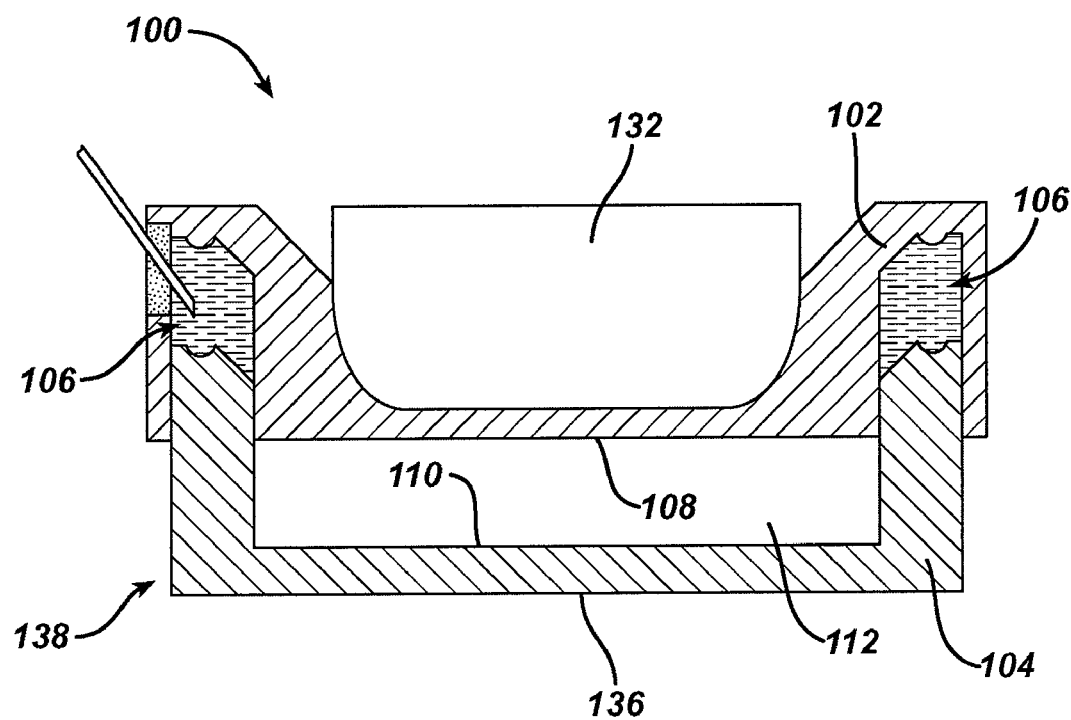
FIG. 6 is a cross-sectional schematic view of an embodiment of an implantable sensor housing having fluid disposed in an internal cavity of the housing.

The housing 100 illustrated in FIG. 6 is similar to the embodiment of FIG. 5 except that the housing 100 in FIG. 6 is a sensor housing (e.g., the sensor housing 60) having a sensor 132 (e.g., the pressure measuring device 64) seated in the housing body 102. Although not shown, the housing body 102 and/or the housing base 104 can include one or more connection members (e.g., the connection member 128) to accommodate catheter connections for the sensor 132 (e.g., the inlet 62a and the outlet 62b).

Figure 7:
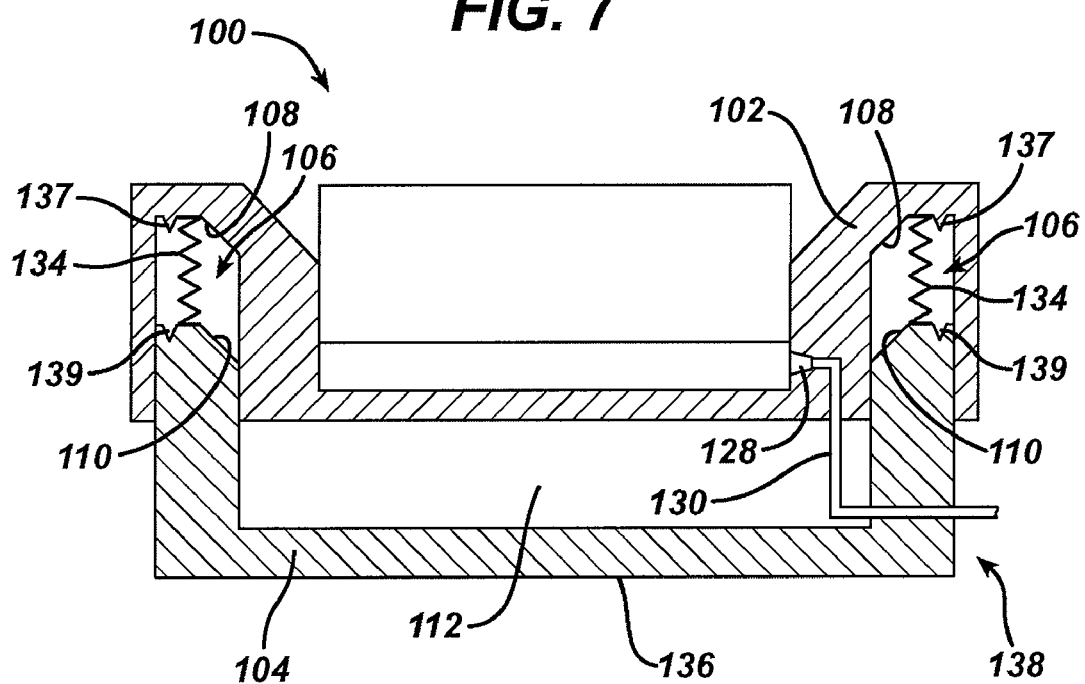
FIG. 7 is a cross-sectional schematic view of an embodiment of an implantable housing having a spring disposed in an internal cavity of the housing.

In some embodiments, the coupling element between the body 102 and the base 104 can include a compliant mechanism that is compressible to decrease the distance between the housing body 102 and the housing base 104. One example of a compliant mechanism is a spring 134, as illustrated in FIG. 7. The spring 134 can include any flexible elastic object having any shape. For example, the spring 134 can include a coil or helical spring having a cylindrical shape as shown in FIG. 7, although the coil spring can have other shapes, such as conical or dual conical, and have individual coils of any shape, such as elliptical or rectangular. Other examples of the spring 134 include an elastic band/thread/cord, a bellows (see FIGS. 11-12, discussed below), a volute spring (see FIGS. 13-14, discussed below), and other similar types of flexible elastic objects. The spring 134 can also have a variety of sizes, and different springs used with the housing 100 can have different sizes (and shapes). The spring 134 can be made from any type of and any combination of material, typically a biocompatible material appropriate for use in a body, such as a polymer, biocompatible metal, and other similar types of material.

As shown in FIG. 7, the spring 134 is disposed in the internal cavity 106 and extends between the interior surface 108 of the body 102 and the interior surface 110 of the base 104. Alternatively or in addition, the spring 134 can extend between the interior surface 108 of the body 102 and the interior surface 110 of the base 104 in the second internal cavity 112. The spring 134 as shown includes two individual springs located on opposite sides of the cylindrical housing 100, but any number of springs can extend between the body 102 and the base 104. For example, one or more springs can be disposed at intervals (which can be equal or variable between any two or more springs) inside the internal cavity 106 around the perimeter of the housing 100. As another example, the spring 134 can be disposed as illustrated in FIG. 7 with an additional spring centrally located in the second external cavity 112 extending between the interior surfaces 108, 110.

The spring 134 has at least two successive positions: expanded and collapsed. The spring 134 typically begins in the expanded position in which it is biased to maintain a substantially constant distance between the body 102 and the base 104. One or more compressions can be applied to the spring 134 to compress the spring 134 to the collapsed position, thereby decreasing the height of the housing 100 to its lowest profile. The spring 134 can have one or more successive positions between the expanded and collapsed positions such that one or more compressions applied to the spring 134 can align and maintain the spring 134 in partially collapsed position(s) between its expanded and collapsed positions, thereby allowing the housing 100 to lower in height with each successive position.

Compressions can be applied to the housing 100 in a variety of ways, such as by applying pressure to the body 102 and/or the base 104 from inside and/or outside the patient's body. The housing 100 is typically compressed by a physician to help prevent injury to the patient and to ensure continued proper functioning of the housing 100.

The housing 100 can include a safety mechanism that must be changed from a locked to an unlocked position before pressure applied to the body 102 and/or the base 104 can change the profile of the housing 100. Examples of safety mechanisms include a mechanical or electrical lock included on or in the housing 100 that a physician can physically manipulate through an incision in the patient or non-invasively manipulate using an electronic device placed against the patient's skin near the location of the housing 100.

When the spring 134 has been compressed to a degree such that the interior surface 108 of the body 102 and the interior surface 110 of the base 104 are in sufficient proximity of each other, a locking mechanism, such as corresponding protrusions 137 and depressions 139, can engage and lock the body 102 and the base 104 together as described above. In some embodiments, one or more compressions of the spring 134 can cause the spring 134 to break, allowing the housing 100 to decrease in height. The broken spring can remain inside the internal cavity 106 with ends still attached to the interior surface 108 of the body 102 and the interior surface 110 of the base 104. With the spring 134 broken, the body 102 and the base 104 can be compressed together and lock via a locking mechanism.

The housing 100 shown in FIG. 7 also includes the connection member 128 coupled to the housing body 102. In this embodiment, the catheter 130 extends through the housing body 102, the second internal cavity 112, and the housing base 104, exiting the housing 100 from the proximal portion 138 of the housing base 104 rather than from the housing body 102. Such a configuration can allow the catheter 130 to extend outside the housing 100 for a shorter distance, thereby reducing chances of catheter snagging, tangling, and rupture, because the housing body 102 and the housing base 104 can be separated by thick subcutaneous fat tissue, with the housing base 104 nearer the next destination of the catheter 130 (e.g., a sensor housing) than the housing body 102.

Another example of a coupling element is any element that can be movable between a first position, in which the housing 100 has a first height, and a second, successive position, in which the housing 100 has a second height that is different from the first height. The coupling element can also be movable between one or more successive positions before and/or after moving from the first to the second position such that the housing's height lowers with each successive position. One example of such a coupling element is a tab 140, shown in FIG. 8. The tab 140 can include at least one flexible tab extending between the body 102 and the base 104 that can maintain the housing 100 in at least one of the successive positions. The tab 140 can have any size and any shape. For example, the tab 140 can include a rod, a flap, and other similar types of elliptical, rectangular, linear, or otherwise shaped elements having two or three dimensions. The tab 140 can be made from any type of and any combination of material, typically a biocompatible material appropriate for use in a body.

Figure 8:
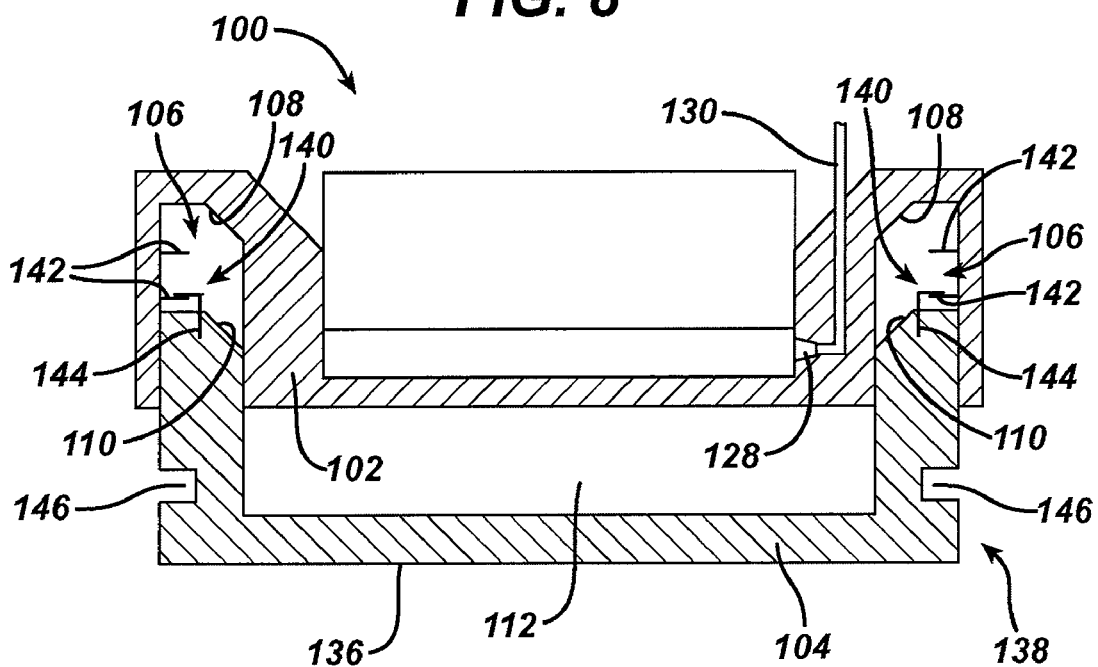
FIG. 8 is a cross-sectional schematic view of an embodiment of an implantable housing having a flexible tab disposed in an internal cavity of the housing.

The tab 140 is disposed in the internal cavity 106 and extends between the interior surface 108 of the body 102 and the interior surface 110 of the base 104. Two tabs 140 are illustrated in FIG. 8 on opposite sides of the housing 100, but the housing 100 can include any number of tabs in any configuration.

In this embodiment, the tab 140 includes a tab body portion 142 and an L-bracket 144. The housing 100 can include any number of tab body portions 142 and any number of L-brackets 144, where one L-bracket 144 can be associated with one or more tab body portions 142. The tab body portion 142 is coupled to the interior surface 108 of the housing body 102, which it extends from in a substantially perpendicular direction, although it can extend in any direction that allows it to engage the L-bracket 144. The L-bracket 144 extends from the interior surface 110 of the housing base 104 in a substantially perpendicular direction and angles toward the interior surface 108 of the housing body 102 to allow engagement with the tab body portion 142 in a lock-step fashion.

The tab 140 has at least two positions. The tab 140 is illustrated in a first position, with the L-bracket 144 engaging a distal-most tab body portion 142. The housing base 104 can be compressed toward the housing body 102, as described above, thereby disengaging the tab body portion 142 and the L-bracket 144 and putting the tab 140 into a second position that provides a lower housing profile than the tab 140 in the first position. When the housing 100 is compressed, the interior surfaces 108, 110 approach each other and the L-bracket 144 can engage another tab body portion 142 (if the body 102 includes more than one tab body portion 142). The tab body portion 142 is typically made from a flexible material that can flex to disengage from the L-bracket 144, and the L-bracket 144 can also or instead be made from a flexible material to help engage/disengage the tab portion 142. If there are no tab body portions for the L-bracket 144 to engage as the housing body 102 and housing base 104 are compressed together, the housing body 102 and the housing base 104 can compress together to engage a locking mechanism, also as described above.

In this embodiment, the locking mechanism includes the tab 140, more specifically the tab body portion 142, and a slot 146 formed in, cut out from, or otherwise present in the outer surface 136 of the housing base 104 (or on the interior surface 110 of the housing base 104, depending on the position of the tab body portion 142 on the housing body 102). The tab body portion 142 can engage the slot 136, thereby locking the housing body 102 and the housing base 104. The slot 146 is typically in the proximal portion 138 of the housing base 104. If the housing 100 includes two or more tabs 140, any number of the tabs 140 can have a corresponding slot 146, although one slot 146 to engage one tab 140 can be enough to lock the housing 100.

Figure 9:
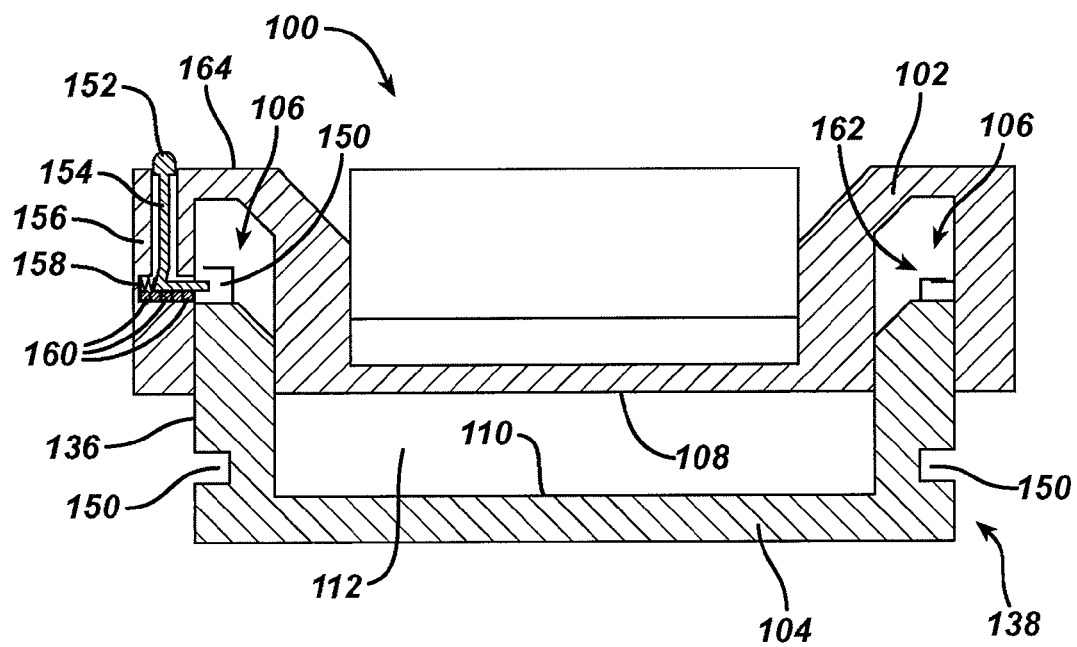
FIG. 9 is a cross-sectional schematic view of an embodiment of an implantable housing having a depressible element.

A movable tab 148, shown in FIG. 9, is another example of a coupling element that can be movable between a first position, in which the housing 100 has a first height, and a second, successive position, in which the housing 100 has a second height that is different from the first height, with any number of successive positions before and/or after the first and second positions. The movable tab 148 can be a tab as described above with respect to FIG. 8 having any size, any shape, any number and configuration on the housing 100, and any material composition. Similar to the tab body portion 142, the movable tab 148 can engage one or more slots 150, similar to the slot 146 of FIG. 8. Unlike the tab body portion 142, however, the movable tab 148 is coupled to a depressible element 152 at least partially extending outside the housing body 102 that can be depressed to move the movable tab 148 from the first position to the second position (and any other possible successive positions). In other words, the depressible element 152 can be depressed to compress the housing body 102 and the housing base 104 together by moving the movable tab 148 such that the movable tab 148 can engage one or more slots 150.

The depressible element 152 can have a variety of configurations that allow it to move the movable tab 148. In the illustrated embodiment, the depressible element 152 includes a button formed on the housing body 102, although the button can be formed anywhere on the housing 100. The housing 100 typically includes one depressible element 152 as shown, although the housing 100 can include any number of depressible elements 152. The depressible element 152 is at least partially accessible outside the housing 100 whether or not it extends beyond the housing body's posterior surface 164. If the depressible element 152 does not extend beyond the housing body's posterior surface 164, which it may not to reduce chances of accidental depression of the depressible element 152, then an instrument such as a needle can be used to depress the depressible element 152.

The depressible element 152 can be coupled to the movable tab 148 via an elongate shaft 154. The elongate shaft 154 can extend from the depressible element 152 and into a bore 156 formed in the housing body 102. The movable tab 148 can couple to the elongate shaft 154 inside the bore 156 and extend into the internal cavity 106 where it can engage the slot 150. In this embodiment, the elongate shaft 154 directly engages the movable tab 148, but in some embodiments, one or more additional elements can be included between the elongate shaft 154 and the movable tab 148. Moreover, one or more additional movable tabs can be coupled to the elongate shaft 154 and move similar to the movable tab when the depressible element 152 is depressed. A spring 158 (which can have any configuration, as described above for the spring 134 of FIG. 7) disposed in the bore 156 and coupled to the movable tab 148 can provide tension sufficient hold the movable tab 148 in position within the internal cavity 106 and the bore 156 when the depressible element 152 is in an uncompressed position. The depressible element 152 can be removably or fixedly coupled to the elongate shaft 154.

Depressing the depressible element 152 can also depress the elongate shaft 154. The elongate shaft 154, when depressed, can slidably move the movable tab 148 along one or more bearings 160 (or other slidable element) in a direction away from the internal cavity 106 and toward the bore 156 such that the spring 158 compresses. Although five bearings 160 are shown, any number of bearings 160 can be disposed in the bore 156. Fully depressing the depressible element 152 can provide enough slidable motion of the movable tab 148 to disengage the movable tab 148 from the slot 150, although in other embodiments a partial depression of the depressible element 152 can disengage the movable tab 148 from the slot 150. The movable tab 148 is typically made from a rigid enough material so it cannot disengage from the slot 150, e.g., if the housing 100 is physically compressed, without depression of the depressible element 152 allowing it to move out of the slot 150. With the movable tab 148 disengaged from the slot 150 and in another position, the housing body 102 and the housing base 104 can be compressed together as described above. The depressible element 152 can be released from depression, thereby releasing tension from the spring 158 and allowing the movable tab 148 to slide along the bearings 160 toward the internal cavity 106. When one of the slots 150 becomes properly aligned with the movable tab 148, the movable tab 148 can engage the slot 150 and be in another position that provides another housing profile. Proper slot 150 to tab 148 alignment can occur either before or after the depressible element 152 has been released because the outer surface 136 of the housing base 104 can prevent the movable tab 148 from moving into the internal cavity 106 until one of the slots 150 is properly aligned with the movable tab 148.

The housing 100 can include one or more coupling elements in addition to the movable tab 148. The additional coupling element(s) can have any configuration, although typically at least one additional coupling element is located on an opposite side of the housing 100 from the movable tab 148 to help maintain a level housing profile. For example, as shown in FIG. 9, the housing 100 can include a tab 162 as described above with reference to FIG. 8, that can engage one or more slots 150 as the housing body 102 and the housing base 104 are compressed together. The number of available slots 150 is typically the same for the movable tab 148 and for any other tabs coupled to the housing body 102 (e.g., the tab 162) to help maintain a level housing profile.

Figure 10:
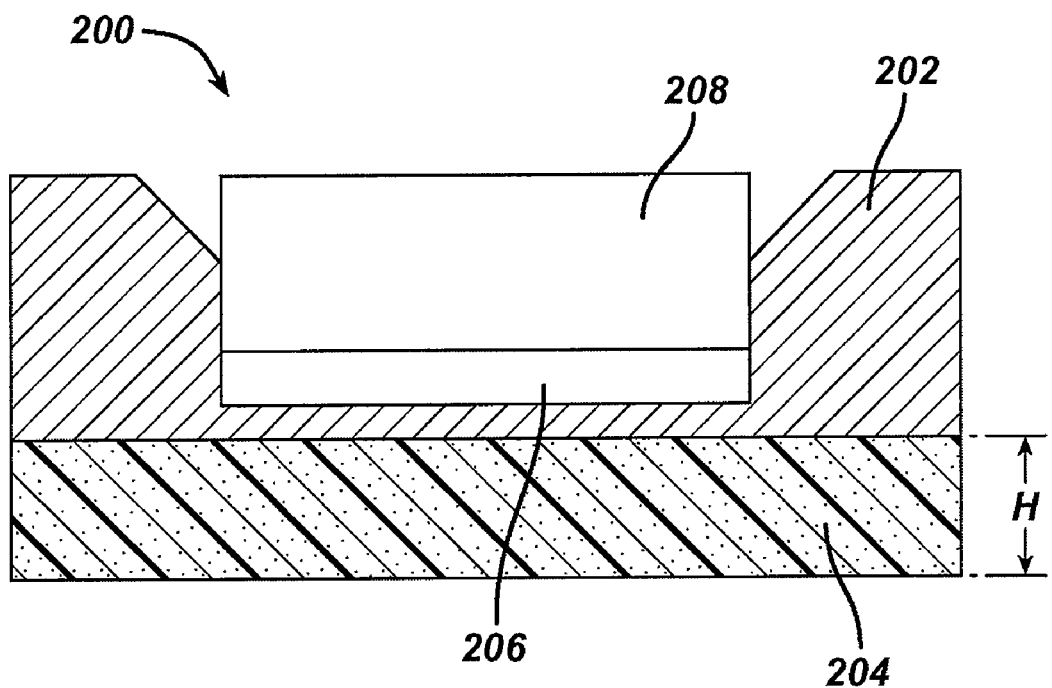
FIG. 10 is a cross-sectional schematic view of an embodiment of an implantable housing at least partially formed from a bioabsorbable material.

FIG. 10 illustrates another embodiment of a housing 200 at least partially formed from a bioabsorbable material operable to adjust the height of the housing 200 over time. The bioabsorbable material can degrade within the patient, thereby lowering the profile of the housing 200 in proportion to the degradation. The housing 200 includes a body 202 formed from a biocompatible material appropriate for use in a body and a base 204 formed from a bioabsorbable material. The bioabsorbable material can degrade uniformly (e.g., bulk hydrolysis) or proportionally to its surface area. Examples of bioabsorbable materials include bioabsorbable polymers such as polylactides (PLA), polyglycolides (PGA), poly(lactide-co-glycolides) (PLGA), polyanhydrides, polyorthoesters, and other similar types of materials that can break down inside a patient and be absorbed or otherwise safely processed by the patient's body.

Any amount of bioabsorbable material can be used to form the base 204 having any height H. The height H generally corresponds to a desired distance between the fascia where the housing 200 is fixed to the patient and the implantable restriction element seated in the body 102, which in this embodiment is a port including a reservoir 206 and a septum 208. As the bioabsorbable material of the base 204 is reabsorbed, the height H of the base 204 can decrease, thereby moving the housing 200 from a maximum height to a minimum height, with any number of successive heights in between. The bioabsorbable material can degrade to allow different heights over any period of time, e.g., two to three years after implantation.

Other embodiments of a housing 300, illustrated in various configurations in FIGS. 11-16, include a housing body 302 a housing base 304, and at least one coupling element 306 extending between the body 302 and the base 304 that can be operable to alter a distance between the body 302 and the base 304 to adjust the height of the housing 300. A locking mechanism can engage and lock the housing body 302 and the housing base 304 together as described above. The coupling element 306 in these embodiments need not be substantially disposed in the housing body 302 or the housing base 304. Rather, the coupling element 306 can couple outside surfaces of the housing body 302 and the housing base 304, such as at their respective interior surfaces 308, 310. A portion of the coupling element 306 can extend into the housing body 302 and/or the housing base 304 when the housing 300 has any height, but typically, at least when the housing 300 is at its maximum height, substantially all of the coupling element 306 is disposed outside the housing body 302 and the housing base 304. Fat tissue can be compacted around the coupling element 306 when it is implanted to help maintain the coupling element's position and to help allow lost weight to alter the coupling element's position. Although not shown in FIGS. 11-16, the coupling element 306 can include a protective sheath disposed around at least a portion of its exterior surface, similar to a bellows. The coupling element 306 (and its sheath, if present) can be made from any biocompatible material appropriate for use in a body.

The housing 300 can also include a connection member 312 (e.g., the catheter tube connection member 36) that can couple to the housing body 302 and to a catheter 314 (e.g., the catheter 50). The connection member 312 is shown in a lateral configuration extending horizontally from the housing body 302 in FIGS. 13-14, but the connection member 312 can have other configurations on the housing body 102. For example, as illustrated in FIGS. 11-12, the connection member 312 can extend vertically from the interior surface 308 of the housing body 302.

Figure 11:
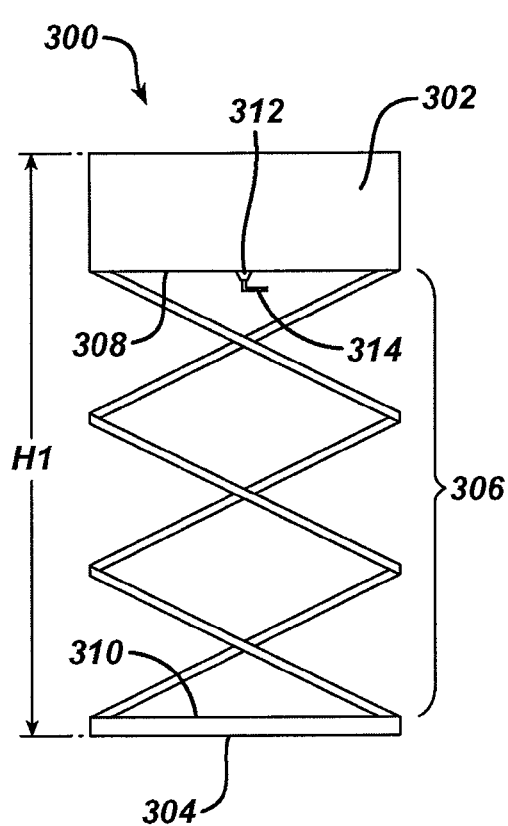
FIG. 11 is a schematic view of an embodiment of an implantable housing having a collapsible structure, shown in an expanded position.
Figure 12:
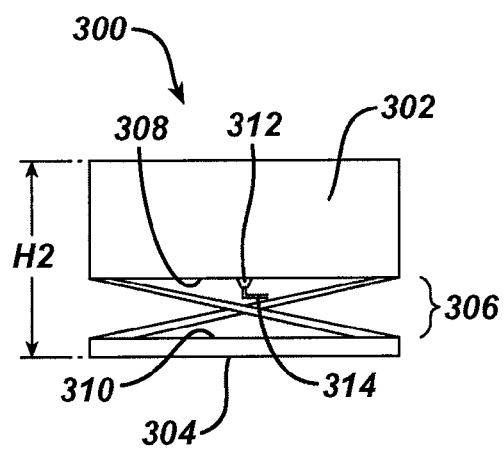
FIG. 12 is a schematic view of the implantable housing of FIG. 11 showing the collapsible structure in a collapsed position.

One embodiment of the coupling element 306 includes a compliant mechanism, e.g., a collapsible structure, that has an expanded position, as illustrated in FIG. 11 where the housing 300 has a height H1, and a collapsed position, as shown in FIG. 12 where the housing 300 has a height H2 that is less than the height H1. Another embodiment of the coupling element 306 includes a compliant mechanism illustrated in FIGS. 13 and 14 that includes a collapsible structure similar to that shown in FIGS. 11 and 12. (H1 and H2 need not represent the same heights in FIGS. 11-12 and FIGS. 13-14.) The coupling element 306 in FIGS. 11-14, described further below, can include any flexible object having any configuration, as described above regarding the spring 134 of FIG. 7. As the patient loses weight, the coupling element 306 can collapse as fat tissue supporting it dissipates. The coupling element 306 can also or instead be manually compressed, such as described above regarding the spring 134. In positions where the housing 300 has a height less than its maximum height, some or all of the coupling element 306 can collapse into the housing base 302, the housing body 304, and/or itself. For example, from the position shown in FIG. 13, the coupling element 306 has nested into itself to have the position shown in FIG. 14.

Figure 15:
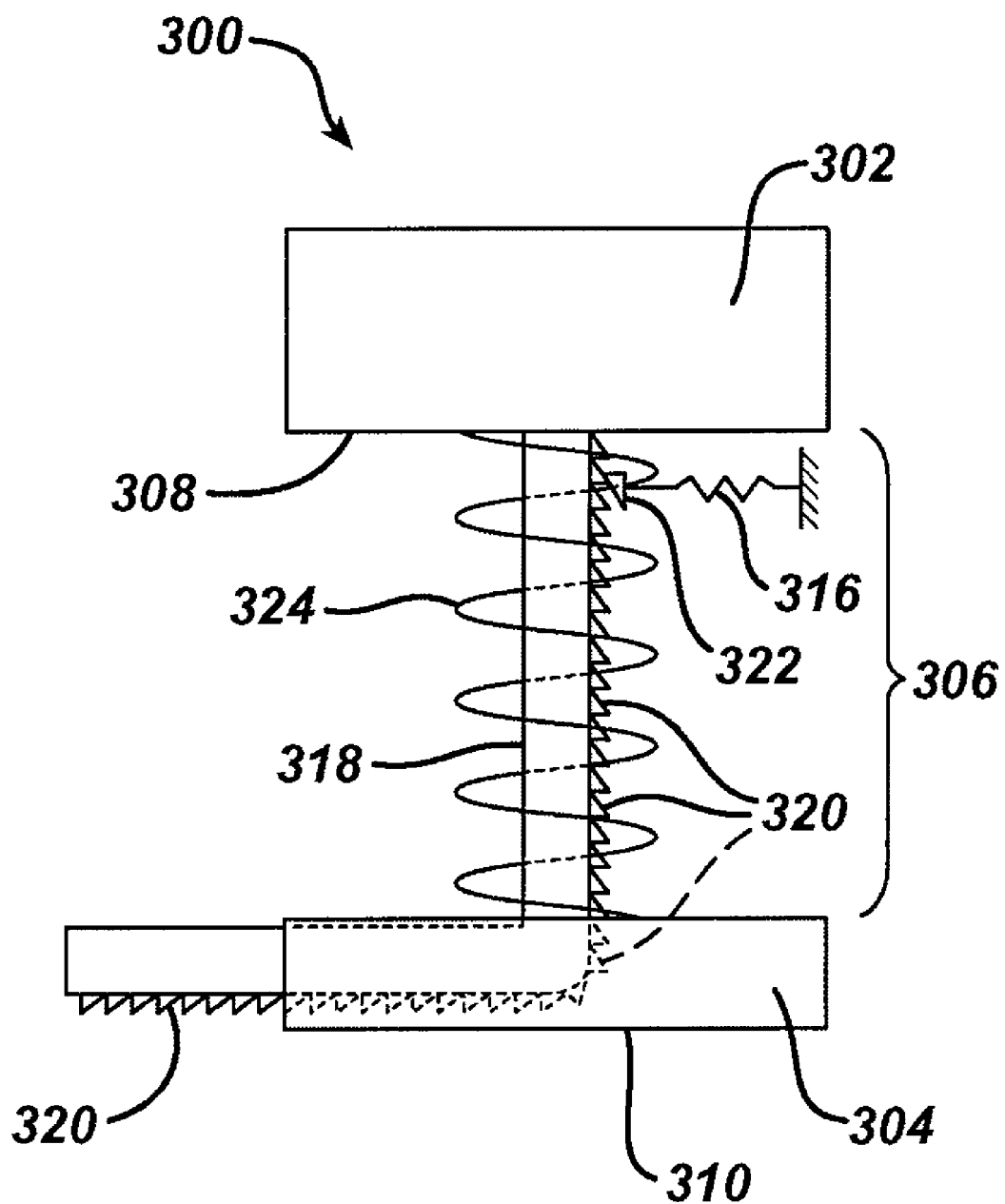
FIG. 15 is a schematic view of an embodiment of an implantable housing having a rack that can be engaged by a pawl.

In another embodiment of the housing 300, illustrated in FIG. 15, the coupling element 306 includes a compliant mechanism such as a spring 316 (e.g., a spring as described above regarding the spring 134 of FIG. 7) that is compressible to decrease the distance between the housing body 302 and the housing base 304. The coupling element 306 also includes a rack 318 having a plurality of teeth 320. The rack 318 can be coupled to the spring 316 via a pawl 322 that can engage the teeth 320 for maintaining the housing 300 at a selected height.

The rack 318 can have any configuration that allows for height adjustment of the housing 300. In the illustrated embodiment, the rack 318 extends between the interior surface 308 of the housing body 302 and the interior surface 310 of the housing base 304 as a substantially rectangular box-shaped structure, although the rack 318 can have any two-dimensional or three-dimensional shape. The rack 318 can also have any size. The rack 318 can also include a support, such as a spring 324 (e.g., a spring as described above regarding the spring 134 of FIG. 7), to help provide stability between the housing body 302 and the housing base 304. The rack 318 can be made of any type of and any combination of rigid and/or flexible material, typically a biocompatible material appropriate for use in a body.

If the rack 318 is made from a flexible material, the rack 318 can be redirected through the housing base 304 as the housing's height changes, as illustrated with dotted lines inside the housing base 304 and with solid lines outside a left surface of the housing base 304. The rack 318 can, however, be redirected to extend outside any surface of the housing base 304. The rack 318 can also be disposed within the housing base 304 before and/or after redirection. For example, the housing 300 may not be sufficiently collapsed to include a redirected rack portion inside the housing base 304. As another example, for any given height of the housing 300, the housing base 304 can be of sufficient size to contain the rack 318 and/or the rack 318 can be sufficiently flexible to be redirected within the housing base 304.

The teeth 320 coupled to the rack 318 can also have any shape and size and be composed of any, typically biocompatible, material. The teeth 320 can be oriented on the rack 318 to, along with the pawl 322, allow motion of the rack 318 in a desired direction, e.g., a direction to decrease the housing's height. The pawl 322 can include any protrusion that can engage the teeth 320 to maintain the housing 300 at a selected height. The pawl 322 can rest against a surface of any one of the teeth 320 to maintain housing height and be movable between one or more of the other teeth 320 to change the housing's profile. The spring 316 coupling the pawl 322 to the patient, along with the shapes of the teeth 320 and the pawl 322, can provide bias against motion of the rack 318 opposite to the desired direction. Although the spring 316 and the rack 318 are shown oriented substantially perpendicular to each other in a resting, non-motion position, the spring 324 and the rack 318 can be oriented with respect to each other in any direction that can allow the pawl 322 to engage the teeth 320 and the housing 300 to change height.

Figure 16:
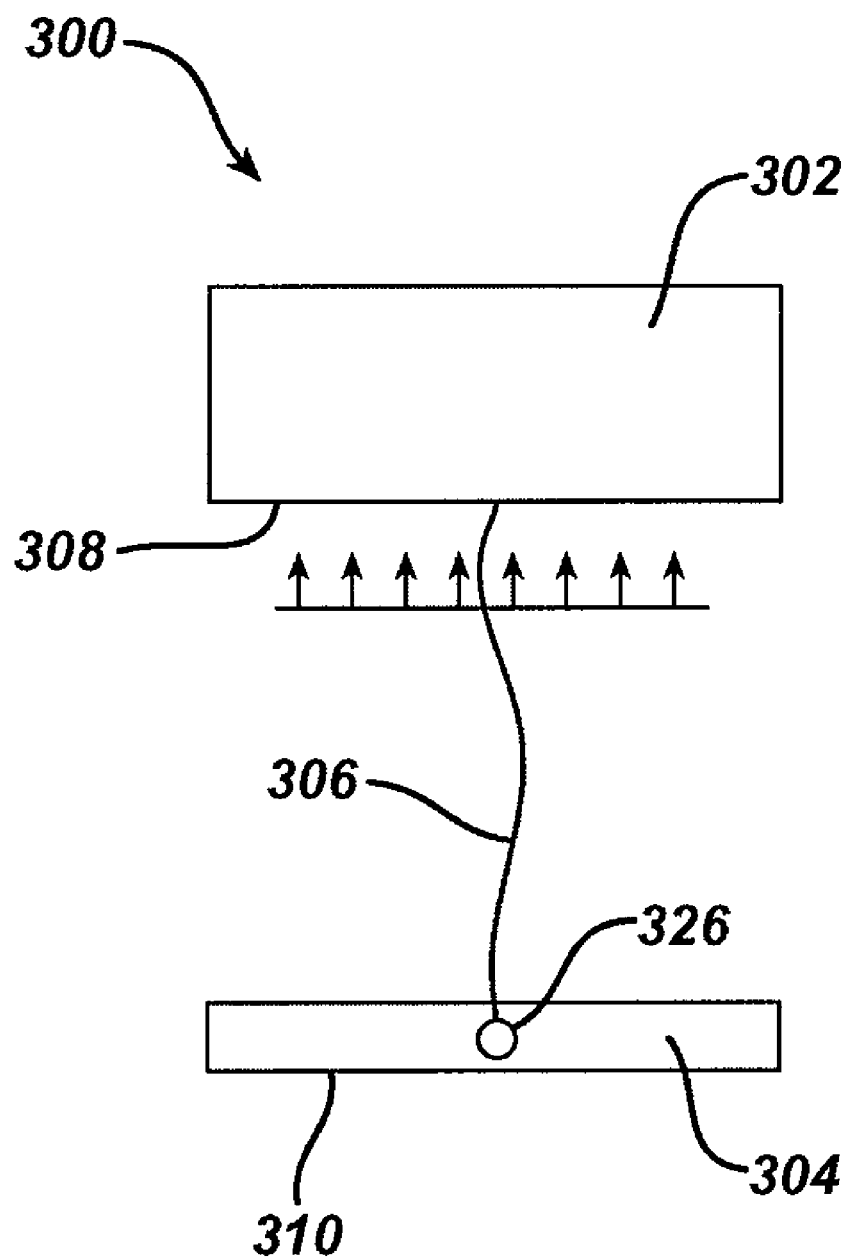
FIG. 16 is a schematic view of an embodiment of an implantable housing having a retractable cord.

FIG. 16 illustrates still another embodiment of the housing 300 where the coupling element includes a retractable cord 306 coupling the housing body 302 and the housing base 304 at their interior surfaces 308, 310, although the retractable cord 306 can be coupled to any surfaces of the housing body 302 and the housing base 304. The retractable cord 306 can include any flexible elastic cord (e.g., string, thread, band, fiber, etc.) having any shape and any length. The retractable cord 306 can be made from any type of and any combination of material, typically a biocompatible material appropriate for use in a body. The patient's fat or tissue can provide a force to maintain separation of the housing base 304 and the housing body 302, as shown by directional arrows in FIG. 16. The force can maintain the retractable cord 306 in a particular position (e.g., maintain the retractable cord 306 at a certain length). As the patient loses weight, the force on the retractable cord 306 can change, thereby allowing the retractable cord 306 to retract into the housing body 304 and allow the housing 300 to change height.

The retractable cord 306 can be disposed inside the housing base 304 in variety of ways. For example, as shown in this embodiment, the retractable cord 306 can coil around a reel 326 disposed inside the housing base 304 and coupled to one end of the retractable cord 306. The reel 326 in this embodiment is substantially elliptical and made from a rigid, biocompatible material, but the reel 326 can have any shape, size, and composition. The reel 326 can also have any orientation within the housing base 304 where the retractable cord 306 extends outside the housing base 304 in a direction substantially parallel to the reel's plane. As another example, in other embodiments, the retractable cord 306 can accordion fold inside the housing base 304.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of forming a restriction in a patient, comprising:
   implanting a restriction device in a patient to form a restriction;
   implanting a housing coupled to the restriction device within the patient such that a base defining a distal external surface of the housing and a body defining a proximal external surface of the housing are spaced a distance apart from one another; and
   adjusting the distance between the proximal and distal external surfaces to lower a profile of the housing implanted within the patient, wherein adjusting the distance comprises changing a volume of fluid within a fluid-filled chamber extending between the base of the housing and the body of the housing to alter the distance between the base and the body, wherein changing the volume of the fluid within the fluid-filled chamber does not alter a volume of a second fluid within the restriction device or change an amount of restriction.

2. The method of claim 1, wherein the restriction device comprises a gastric band that is implanted around a patient's stomach.

3. The method of claim 1, wherein the restriction device is coupled to the housing by a catheter.

4. The method of claim 1, wherein adjusting the distance comprises causing the body of the housing to move relative to the base of the housing.

5. The method of claim 1, wherein adjusting the distance comprises inserting a needle through tissue and into a fill port formed in the housing, and changing the volume of fluid within the housing.

6. The method of claim 1, wherein the housing includes a pressure sensor that senses a pressure of fluid within the implantable restriction device and that communicates pressure data to an external monitor.

7. The method of claim 1, wherein implanting the housing comprises positioning the body of the housing a first distance from a skin surface of the patient, and securing the base of the housing to tissue of the patient a second distance from the skin surface, the second distance being greater than the first distance.

8. The method of claim 7, wherein adjusting the distance substantially maintains the body of the housing at the first distance from the skin surface, and causes the base of the housing to move toward the skin surface such that the second distance decreases.

9. The method of claim 1, wherein changing the volume of the fluid comprises removing an amount of the fluid from the fluid-filled chamber to decrease the distance between the base and the body.

10. A method of forming a restriction in a patient, comprising:
    implanting a restriction device in a patient to form a restriction;
    implanting a housing coupled to the restriction device within the patient such that a base defining a distal external surface of the housing and a body defining a proximal external surface of the housing are spaced a distance apart from one another;
    adjusting the distance between the proximal and distal external surfaces to lower a profile of the housing implanted within the patient; and
    adjusting a volume of fluid within the restriction device to change an amount of restriction, wherein adjusting the volume of the fluid within the restriction device does not alter the distance between the proximal and distal external surfaces.

11. A method of forming a restriction in a patient, comprising:
    implanting a gastric band around a patient's stomach to restrict fluid flow through the stomach, the gastric band having a catheter extending therefrom, the catheter extending between the gastric band and a housing that is implanted in an abdomen of the patient beneath a tissue surface such that a first fluid can flow through the catheter between the gastric band and the housing; and
    changing a volume of a second fluid within the housing to move a body of the housing relative to a base of the housing and thereby adjust a height of the housing, wherein changing the volume of the second fluid does not alter an amount of the first fluid that can flow through the catheter between the gastric band and the housing.

12. The method of claim 11, wherein changing the volume of the second fluid comprises removing an amount of the second fluid from the housing such that the height of the housing decreases.

13. The method of claim 12, wherein removing the amount of the second fluid causes the base to occupy an internal space in the housing formerly containing the removed amount of the second fluid.

14. The method of claim 12, wherein removing the amount of the second fluid causes the base and the body to lock together.

15. The method of claim 11, further comprising changing a volume of the first fluid within the gastric band to change an amount of restriction, wherein changing the volume of the first fluid does not alter the volume of the second fluid within the housing.

16. The method of claim 11, wherein the first fluid is contained within a reservoir of the housing, the second fluid is contained within an internal cavity of the housing, and the reservoir and the internal cavity are not in fluid communication with one another.

* * * * *